United States Patent [19]

Wehinger et al.

[11] Patent Number: 4,798,840
[45] Date of Patent: Jan. 17, 1989

[54] CORONARY-ACTIVE FLUORINE-CONTAINING 1,4-DIHYDROPYRIDINES

[75] Inventors: Egbert Wehinger; Horst Meyer; Andreas Knorr; Stanislav Kazda, all of Wuppertal, Fed. Rep. of Germany

[73] Assignee: Bayer Aktiengesellschaft, Leverkusen, Fed. Rep. of Germany

[21] Appl. No.: 937,764

[22] Filed: Dec. 4, 1986

[30] Foreign Application Priority Data

Dec. 13, 1985 [DE] Fed. Rep. of Germany ....... 3544211

[51] Int. Cl.$^4$ .................. A61K 31/455; C07D 211/90
[52] U.S. Cl. .................... 514/356; 514/339; 514/334; 514/338; 514/235.5; 546/321; 546/272; 546/258; 546/271; 544/131
[58] Field of Search ............... 546/321, 283, 284, 231, 546/278, 275, 280, 257, 273, 271, 270, 167, 139, 144; 514/356, 248, 249, 252, 259, 256, 247, 307, 314, 334, 338, 339, 337, 340, 341, 342, 343; 544/238, 333, 405, 284, 353

[56] References Cited

U.S. PATENT DOCUMENTS 4,256,749 3/1981 Horstmann et al. ................ 546/263
4,622,332 11/1986 Wehinger et al. .................. 546/321

FOREIGN PATENT DOCUMENTS 2405658 8/1974 Fed. Rep. of Germany .
2841667 4/1980 Fed. Rep. of Germany .
3208628 9/1983 Fed. Rep. of Germany .

Primary Examiner—Jane T. Fan
Attorney, Agent, or Firm—Sprung Horn Kramer & Woods

[57] ABSTRACT

Hypotensive long-acting 1,4-dihydropyridines of the formula

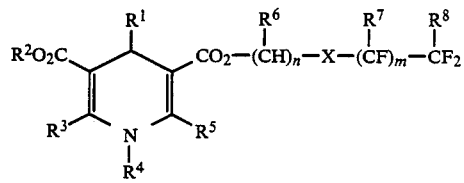

in which
$R^1$ is phenyl or heterocyclic,
$R^2$, $R^3$, $R^4$ and $R^5$ have the usual definitions in such compounds,
$R^6$ represents hydrogen or a lower alkyl radical or the trifluoromethyl group,
$R^7$ and $R^8$ each denote a hydrogen atom or a fluorine atom,
$n \geq 1$ and
$m \geq 0$, and the sum of n and m must be a least 4, and
X represents a single bond, an oxygen atom or the group —N(alkyl)—$O_2S$—, or pharmacologically acceptable acid addition salts thereof.

11 Claims, No Drawings

CORONARY-ACTIVE FLUORINE-CONTAINING 1,4-DIHYDROPYRIDINES

The present invention relates to new 1,4-dihydropyridine derivatives which contain fluorinated carbon atoms in their ester groups, several processes for their preparation and their use as medicaments, in particular as agents which influence the circulation.

It has already been disclosed that diethyl 1,4-dihydro-2,6-dimethyl-4-phenyl-pyridine-3,5-dicarboxylate is obtained when ethyl 2-benzylideneacetoacetate is reacted with ethyl β-aminocrotonate or ethyl acetoacetate and ammonia (E. Knoevenagel, Ber. dtsch. chem. Ges. 31, 743 (1898)).

It is furthermore known that certain 1,4-dihydropyridines have interesting pharmacological properties (F. Bossert, W. Vater, Naturwissenschaften 58, 578 (1971)).

It is moreover known from German Offenlegungsschriften (German Published Specifications) 2,841,667 and U.S. application Ser. No. 468,621, filed Feb. 22, 1983, now pending, that similar compounds can be used as coronary agents, antihypertensive agents and agents for increasing the peripheral circulation.

The present invention relates to new 1,4-dihydropyridine derivatives of the general formula I

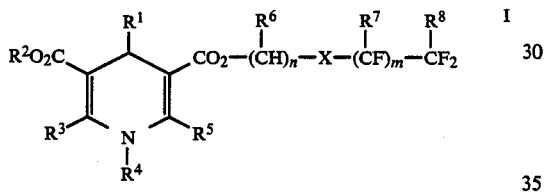

in which
- $R^1$ represents aryl, or represents thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxalyl, it being possible for the aryl radical and the heterocyclic radicals optionally to contain 1 or 2 identical or different substituents from the group comprising phenyl, alkyl, alkoxy, alkylene, dioxyalkylene, halogen, trifluoromethyl, polyfluoroalkoxy, nitro, cyano, azido and $SO_y$-alkyl (y=0 to 2), which can in turn be substituted by fluorine,
- $R^2$ represents a straight-chain, branched or cyclic, saturated or unsaturated hydrocarbon radical which is optionally interrupted by an oxygen or sulphur atom in the chain and/or is optionally substituted by halogen, cyano, hydroxyl, acyloxy, nitro or nitrooxy, or by a phenyl, phenoxy, phenylthio or phenylsulphonyl group, which can in turn be further substituted by halogen, cyano, dialkylamino, alkoxy, alkyl, trifluoromethyl or nitro, or optionally by an α-, β- or γ-pyridyl group, or optionally by an amino group, this amino group carrying two identical or different substituents from the group comprising alkyl, alkoxyalkyl, aryl and aralkyl, and these substituents optionally forming, with the nitrogen atom, a 5- to 7-membered ring which can contain, as a further heteroatom, an oxygen or sulphur atom or the N-alkyl/phenyl grouping, or represents the group

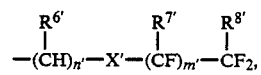

it being possible for this group to be identical to

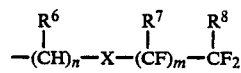

and the definitions of $R^{6'}$, $R^{7'}$ $R^{8'}$, $n'$, $m'$ and $X'$ corresponding to those of $R^6$, $R^7$, $R^8$, n, m and X,
- $R^3$ and $R^5$ are identical or different and each represent hydrogen, a straight-chain, branched or cyclic alkyl radical, an aryl radical or an aralkyl radical, or one of the substituents $R^3$ or $R^5$ represents an alkyl radical, which is in turn substituted by acyloxy, alkoxy, dialkoxy, hydroxyl, amino, aminoalkoxy, phthalimido, phthalimidoalkoxy, piperidinoalkoxy, morpholinoalkoxy or N-aryl-N'-piperazinoalkoxy, or one of the substituents $R^3$ or $R^5$ represents the formyl or nitrile group,
- $R^4$ denotes hydrogen or a straight-chain or branched alkyl radical which is optionally interrupted by one or two oxygen atoms in the alkyl group and/or which is optionally substituted by a piperidine or morpholine radical, or represents an aryl or aralkyl radical,
- $R^6$ represents hydrogen or a lower alkyl radical or the trifluoromethyl group,
- $R^7$ and $R^8$ each denote a hydrogen atom or a fluorine atom,
- $n \leq 1$ and
- $m \leq 0$, and the sum of n and m must be at least 4, and
- X represents a single bond, an oxygen atom or the group $-N(alkyl)-O_2S-$, and their pharmaceutically acceptable acid addition salts.

Depending on the nature of the substituents, the compounds according to the invention can exist in stereoisomeric forms, which either behave as mirror images (enantiomers) or do not behave as mirror images (diastereomers). The present invention relates both to the antipodes and to the racemic forms as well as to the diastereomer mixtures.

The compounds according to the invention can be prepared by several processes, which are essentially based on the known Hantzsche 1,4-dihydropyridine synthesis. In the case where the radicals $R^1$, $R^2$, $R^4$, $R^6$, $R^7$, $R^8$ and n, m and X in the general formula I have the above-mentioned meaning and $R^3$ and $R^5$ represent hydrogen or a straight-chain, branched or cyclic alkyl radical, which can in turn be substituted by acyloxy, alkoxy, dialkoxy, phthalimido, phthalimidoalkoxy, piperidinoalkoxy, morpholinoalkoxy or N-phenyl-N'-piperazinoalkoxy, or represent an aryl or aralkyl radical, the compounds according to the invention are prepared by a process in which (A) ylidene-β-keto esters of the general formula II

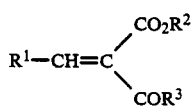

in which $R^1$, $R^2$ and $R^3$ have the abovementioned meaning, are reacted with enaminocarboxylic acid esters of the general formula III

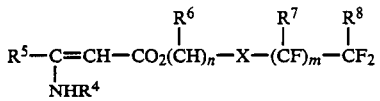  III in which
$R^4$, $R^5$, $R^6$, $R^7$, $R^8$, X, n and m have the above-mentioned meaning,
if appropriate in the presence of inert organic solvents, or (B) ylidene-β-keto esters of the general formula II

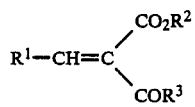  II in which
$R^1$, $R^2$ and $R^3$ have the abovementioned meaning, are reacted with β-ketocarboxylic acid esters of the general formula IV and amines of the general formula V

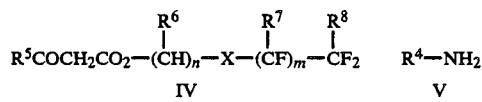

in which
$R^4$, $R^5$, $R^6$, $R^7$, $R^8$, X, n and m have the above-mentioned meaning,
if appropriate in the presence of inert organic solvents, or (C) ylidene-β-keto esters of the general formula VI

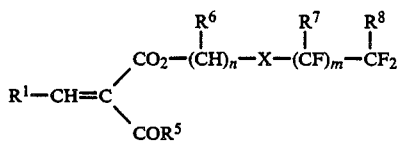  VI in which
$R^1$, $R^5$, $R^6$, $R^7$, $R^8$, X, n and m have the above-mentioned meaning,
are reacted with enaminocarboxylic acid esters of the general formula VII

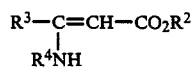  VII in which
$R^2$, $R^3$ and $R^4$ have the abovementioned meaning, if appropriate in the presence of inert organic solvents, or (D) ylidene-β-keto esters of the general formula VI

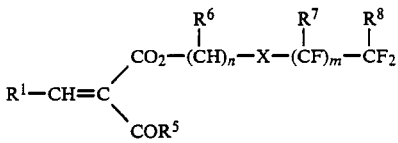  VI in which
$R^1$, $R^5$, $R^6$, $R^7$, $R^8$, X, n and m have the above-mentioned meaning,
are reacted with β-ketocarboxylic acid esters of the general formula VIII and amines of the general formula V

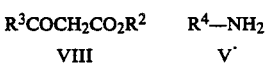  
VIII  V in which
$R^2$, $R^3$ and $R^4$ have the abovementioned meaning,
if appropriate in the presence of inert organic solvents, or (E) aldehydes of the general formula IX $$R^1-C\begin{matrix}H\\ \\O\end{matrix}$$  IX in which
$R^1$ has the abovementioned meaning,
are reacted with enaminocarboxylic acid esters of the general formula III and β-ketocarboxylic acid esters of th general formula VIII $R^5-C(NHR^4)=CH-CO_2(CH)_n-X-(CF)_m-CF_2$ with $R^6, R^7, R^8$ substituents  III $R^3COCH_2CO_2R^2$  VIII in which
$R^2$, $R^3$, $R^4$, $R^5$, $R^6$, $R^7$, $R^8$, X n and m have the abovementioned meaning,
if appropriate in the presence of inert organic solvents, or (F) aldehydes of the general formula IX $$R^1-C\begin{matrix}H\\ \\O\end{matrix}$$  IX in which
$R^1$ has the abovementioned meaning,
are reacted with enaminocarboxylic acid esters of the general formula VII and β-ketocarboxylic acid esters of the general formula IV $R^5COCH_2CO_2-(CH)_n-X-(CF)_m-CF_2$ with $R^6, R^7, R^8$  IV $R^3-C(R^4NH)=CH-CO_2R^2$  VII in which R², R³, R⁴, R⁵, R⁶, R⁷, R⁸, X, n and m have the abovementioned meaning, if appropriate in the presence of inert organic solvents.

(G) It has furthermore been found that the compounds according to the invention are also obtained by a process in which the 1,4-dihydropyrimidinemonocarboxylic acids of the general formulae X and XI

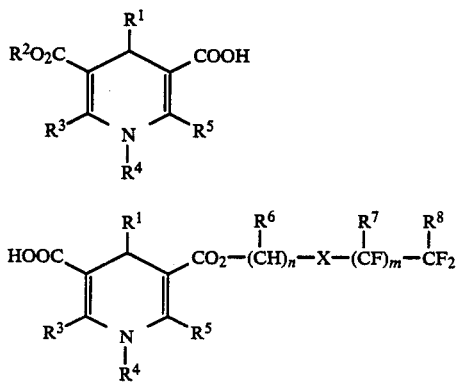

in which

R¹, R², R³, R⁴, R⁵, R⁶, R⁷, R⁸, n and m have the abovementioned meaning, are esterified with alcohols of the general formula XII or XIII

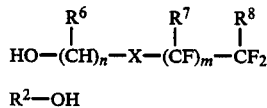

in which

R², R⁶, R⁷, R⁸, X, n and m have the abovementioned meaning, by the customary methods of esterfication of carboxylic acids (for example via the acid chloride or imidiazolide or in the presence of dicyclohexylcarbodiimide).

If optically active enantiomerically pure 1,4-dihydropyridinemonocarboxylic acids of the general formula X or XI in which the particular C₄ carbon atoms of the dihydropyrodine ring represent the sole chirality centers are used, esterification with archiral alcohols of the formulae XII and XIII gives, providing that the ester groups in the end products are different, optically active enantiomerically pure compounds of the general formula I with achiral substituents. It is of course possible, depending on the choice of the optically active starting acids X and XI and of the alcohol components XII and XIII, for compounds according to the invention with additional chirality centers (of uniform configuration) to be obtained by this route.

(H) In the case where the radicals R¹, R², R⁴, R⁶, R⁷, R⁸ and n, m and X in the general formula I have the above-mentioned meaning and R³ or R⁵ represent the formyl or nitrile group, or represent an alkyl radical which is substituted by hydroxyl, amino or aminoalkoxy, the compounds according to the invention are preferably prepared by a process in which suitable intermediate products according to the invention are synthesized by processes (A) to (G) and these are further reacted in subsequent reactions. If R³ or R⁵ represent, for example, a formyl group, these derivatives are obtained by acid hydrolysis of compounds of the general formula I according to the invention in which R³ or R⁵ denote a dialkoxymethyl radical. The derivatives of the general formula I according to the invention where R³ or R⁵ is formyl can be converted into the substances of the general formula I according to the invention where R³ or R⁵ is nitrile by reaction with hydroxylamine and subsequent dehydration of the resulting oxime by methods which are known from the literature.

The compounds of the general formula I according to the invention in which R³ or R⁵ represents an alkyl radical which is substituted by (a) hydroxyl, (b) amino or (c) aminoalkoxy are obtained in a similar manner by a process in which (a) the corresponding acyloxy derivatives according to the invention are hydrolyzed under acid or alkaline conditions, (b) the corresponding phthalimido compounds which can be prepared by the processes described above are hydrazinolyzed, for example, or (c) the corresponding phthalimidoalkoxy derivatives according to the invention are reacted with hydrazine.

The compounds according to the invention have useful pharmacological properties. In particular, because of their potent and long-lasting circulation-influencing action, they can be used as antihypertensive agents, as vasodilators, as cerebral therapeutics and as coronary therapeutics, and are thus to be regarded as an enrichment of pharmacy.

The potent and long-lasting hypotensive action is of particular interest.

Depending on the nature of the starting substances used, the synthesis variants for the compounds according to the invention can be represented by the following equations:

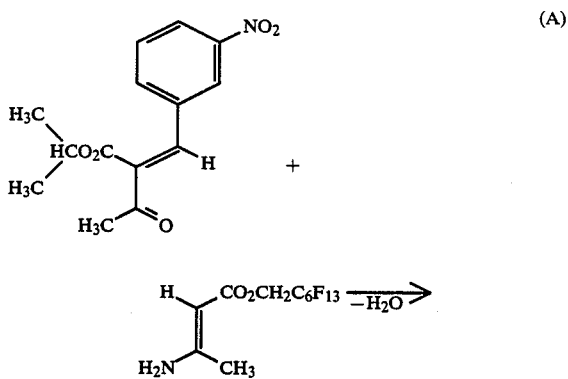

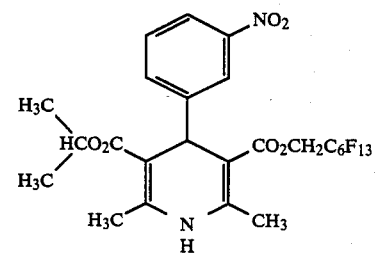

(B)
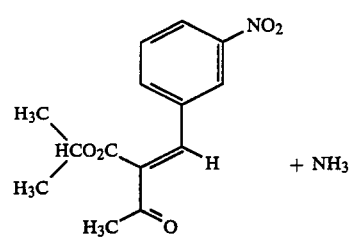
+ NH₃
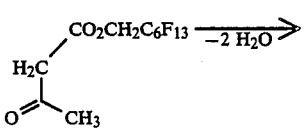 −2 H₂O ⟶
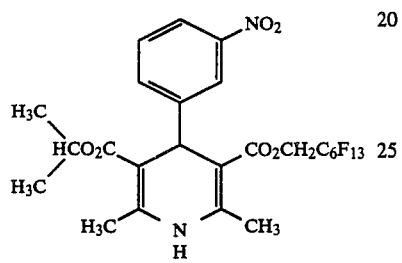
(C)
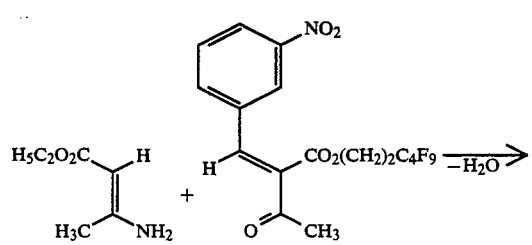 −H₂O ⟶
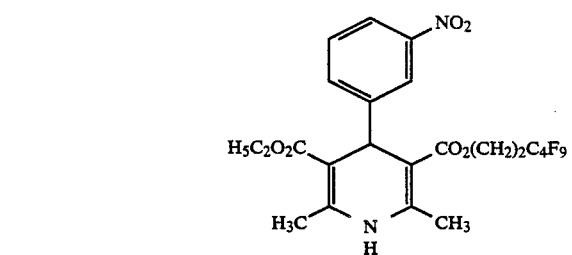
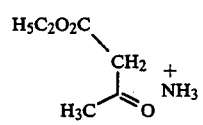 +
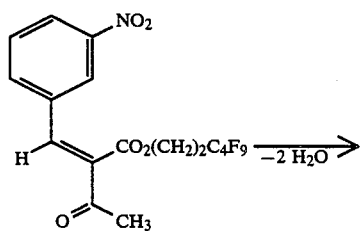 −2 H₂O ⟶
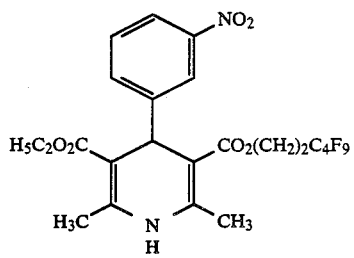
(E)
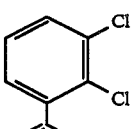 
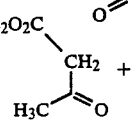 +
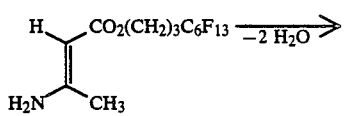 −2 H₂O ⟶
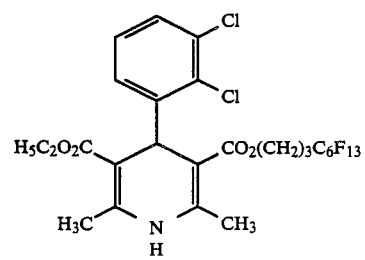
(F)
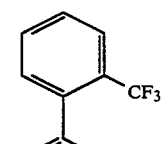 
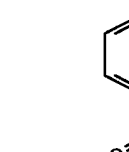 +
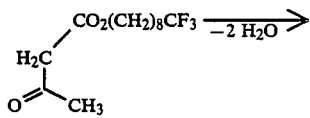 −2 H₂O ⟶
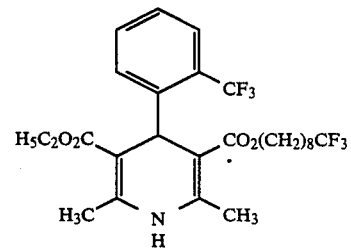

-continued

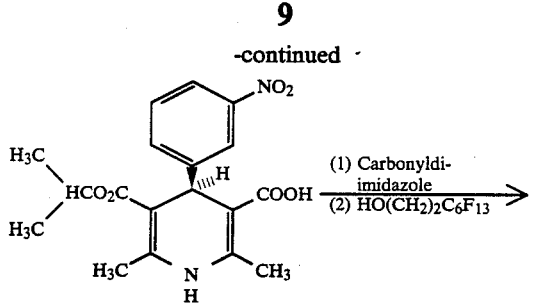  (G)

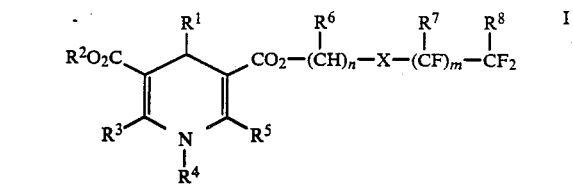

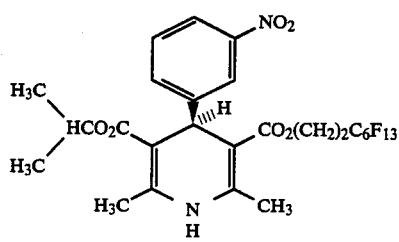

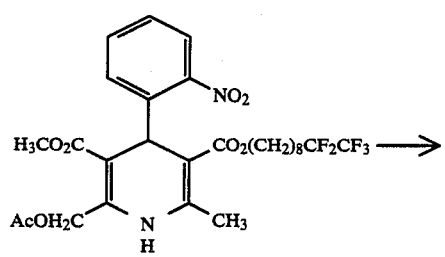  (H)

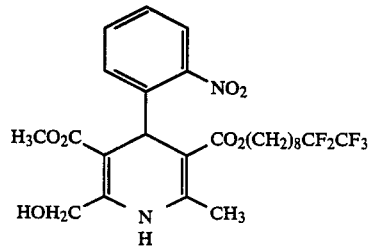

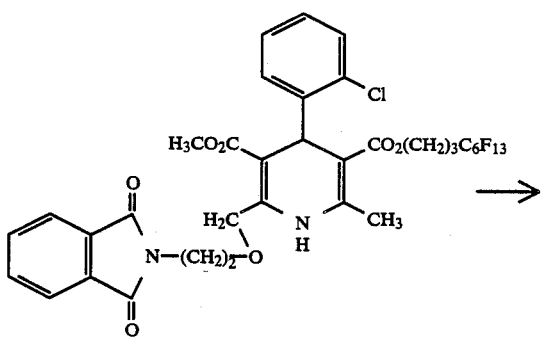

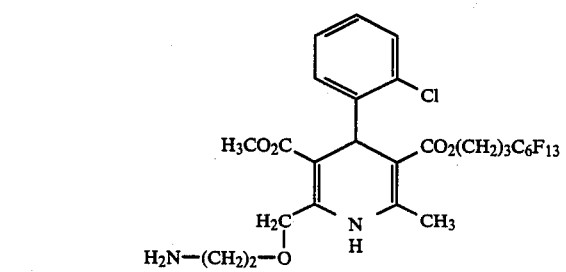

Compounds according to the invention which are of particular interest are those of the general formula I

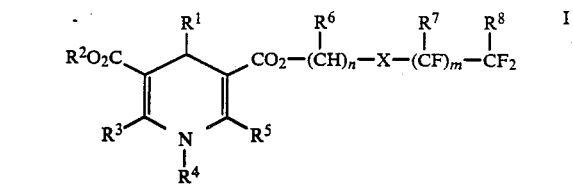

in which

R¹ represents phenyl or naphthyl, or represents thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxalyl, it being possible for the ring systems mentioned in each case to be substituted by 1 or 2 identical or different substituents from the group comprising phenyl, straight-chain or branched alkyl with 1 to 8 carbon atoms, cycloalkyl with 3 to 7 carbon atoms, alkoxy with 1 to 4 carbon atoms, tri-, tetra- and pentamethylene, dioxymethylene, dioxyethylene, halogen, trifluoromethyl, trifluoromethoxy, difluoromethoxy, tetrafluoroethoxy, nitro, cyano, azido and $SO_y$-alkyl, wherein y denotes a number from 0 to 2 and alkyl preferably contains 1 to 4 carbon atoms with optionally 1 to 3 fluorine atoms, R² represents a straight-chain, branched or cyclic, saturated or unsaturated hydrocarbon radical with up to 20 carbon atoms, which is optionally interrupted by an oxygen atom or a sulphur atom in the chain and/or which is optionally substituted by halogen, cyano, hydroxyl, acyloxy, nitro or nitrooxy, or by a phenyl, phenoxy, phenylthio or phenylsulphonyl group which is optionally substituted by halogen, in particular fluorine, chlorine or bromine, cyano, dialkylamino with in each case 1 or 2 carbon atoms per alkyl group, alkoxy with 1 to 4 carbon atoms, alkyl with 1 to 4 carbon atoms, trifluoromethyl or nitro, or by an α-, β- or γ pyridyl group, or by an amino group, this amino group carrying two identical or different substituents from the group comprising alkyl with up to 4 carbon atoms, alkoxyalkyl with up to 4 carbon atoms, phenyl and aralkyl, in particular benzyl, and these substituents optionally forming, with the nitrogen atom, a 5- to 7-membered ring which can contain, as a further heteroatom, an oxygen or sulphur atom or the N-phenyl- or N-alkyl grouping, the alkyl group preferably containing 1 to 3 carbon atoms, or represents the group

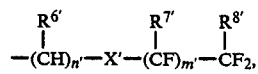

it being possible for this group to be identical to or different from

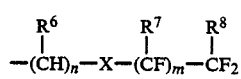

and the definitions of $R^{6'}$, $R^{7'}$, $R^{8'}$, n', m' and X' corresponding to those of $R^6$, $R^7$, $R^8$, n, m and X, $R^3$ and $R^5$ are identical or different and each represent hydrogen, a straight-chain, branched or cyclic alkyl radical with up to 6 carbon atoms or a phenyl or benzyl radical, or one of the substituents $R^3$ or $R^5$ represents an alkyl radical which has up to 6 carbon atoms and is substituted by acetoxy or benzoyloxy, alkoxy or dialkoxy with in each case up to 3 carbon atoms per alkyl group, hydroxyl, amino, aminoalkoxy with up to 6 carbon atoms, phthalimido, phthalimidoalkoxy, piperidinoalkoxy, morpholinoalkoxy or N-phenyl-N'-piperazinoalkoxy with in each case up to 6 carbon atoms per alkoxy group, or one of the substituents $R^3$ or $R^5$ represents the formyl or nitrile group, $R^4$ denotes hydrogen or a straight-chain or branched alkyl radical which has 1 to 4 carbon atoms and which is optionally interrupted by an oxygen atom in the chain and/or which is optionally substituted by a piperidino or morpholino radical, or represents a phenyl or benzyl radical, $R^6$ represents hydrogen or a lower alkyl radical with 1 or 2 carbon atoms, or represents a trifluoromethyl group, $R^7$ and $R^8$ each denote a hydrogen atom or a fluorine atom, n is greater than/equal to 1 and m is greater than/equal to 0, and the sum of n and m must be at least 4, and X represents a single bond, an oxygen atom or the group —N(alkyl)$O_2$S— with 1 to 3 carbon atoms in the alkyl radical.

Preferred compounds which may be mentioned are those of the general formula I

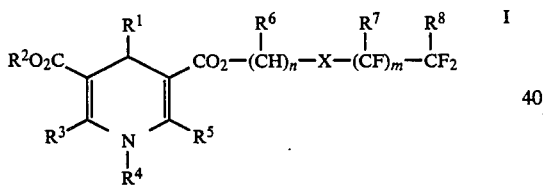

in which $R^1$ represent phenyl, thienyl, furyl, pyridyl, quinolyl or benzoxadiazolyl; the ring systems mentioned optionally being substituted by 1 or 2 identical or different substituents from the group comprising phenyl, alkyl with 1 to 4 carbon atoms, alkoxy with 1 or 2 carbon atoms, dioxymethylene, fluorine, chlorine, bromine and iodine, trifluoromethyl, trifluoromethoxy, difluoromethoxy, trifluoromethylsulphonyl, nitro, cyano, azido and alkylmercapto with 1 to 4 carbon atoms in the alkyl radical, $R^2$ represents a straight-chain, branched or cyclic, saturated or unsaturated hydrocarbon radical which has up to 14 carbon atoms and which is optionally interrupted by an oxygen atom in the chain and/or which is optionally substituted by fluorine, chlorine, bromine, iodine, cyano, hydroxyl, acetoxy or nitrooxy, or by a phenyl or phenoxy group which is optionally substituted by halogen, in particular fluorine or chlorine, alkoxy with 1 to 4 carbon atoms, alkyl with 1 to 4 carbon atoms or trifluoromethyl, or by an α-, β- or γ-pyridyl group, or by an amino group, this amino group carrying two identical or different substituents from the group comprising alkyl with up to 4 carbon atoms, phenyl and aralkyl, in particular benzyl, or represents the group

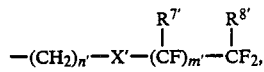

it being possible for this group to be identical to or different from

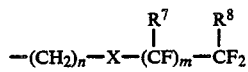

and the definitions of $R^{7'}$, $R^{8'}$, n', m' and X' corresponding to those of $R^7$, $R^8$, n, m and X, $R^3$ and $R^5$ are identical or different and each represent hydrogen, a straight-chain, branched or cyclic alkyl radical with up to 6 carbon atoms or a phenyl or benzyl radical, or one of the substituents $R^3$ or $R^5$ represents an alkyl radical which has up to 4 carbon atoms and is substituted by acetoxy, methoxy or dimethoxy, hydroxyl, amino, phthalimido or aminoalkoxy or phthalimidoalkoxy with in each case up to 4 carbon atoms per alkoxy group, or one of the substituents $R^3$ or $R^5$ represents the formyl or nitrile group, $R^4$ denotes hydrogen or an alkyl radical which has up to 4 carbon atoms and which is optionally interrupted by an oxygen atom in the chain and/or which is optionally substituted by a morpholino radical, or represents a phenyl or benzyl radical, $R^6$ represents hydrogen, $R^7$ and $R^8$ each denote a hydrogen atom or a fluorine atom, n is greater than/equal to 1 and m is greater than/equal to 0, and the sum of n and m represents an integer from 5 to 20, and X represents a single bond or the group —N(CH$_3$)O$_2$S—.

Compounds which are to be especially singled out are the racemic and enantiomerically pure compounds of the general formula I

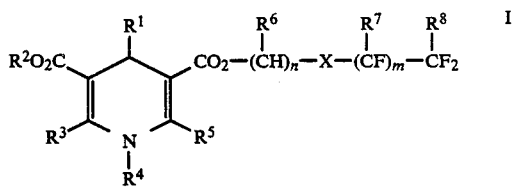

in which $R^1$ represents phenyl, pyridyl or benzoxadiazolyl, these ring systems being substituted by 1 or 2 identical or different substituents from the group comprising chlorine, trifluoromethyl, nitro and cyano, $R^2$ represents a straight-chain, branched or cyclic hydrocarbon radical which has up to 8 carbon atoms and which is optionally interrupted by an oxygen atom in the chain and/or which is optionally substituted by fluorine, cyano, acetoxy, phenyl, phenoxy or α-, β- or γ-pyridyl, or by an amino group, this amino group carrying two identical or different substituents from the group comprising alkyl with up to 4 carbon atoms and benzyl, or represents the group —(CH$_2$)$_n'$—X'—(CF$_2$)$_m'$—CF$_3$, it being possible for this group to be identical to or different from —(CH$_2$)$_n$—X—(CF$_2$)$_m$—CF$_3$ and the definitions of n', m' and X' corresponding to those of n, m and X, R$^3$ and R$^5$ are identical or different and each represent a straight-chain or cyclic alkyl radical with up to 6 carbon atoms, or one of the substituents R$^3$ or R$^5$ represents an alkyl radical which has up to 4 carbon atoms and is substituted by acetoxy, hydroxyl, phthalimido, amino, phthalimidoethoxy or aminoethoxy, or one of the substituents R$^3$ or R$^5$ represents the formyl or nitrile group, R$^4$ represents hydrogen or the morpholinoethyl radical, R$^6$ denotes hydrogen, R$^7$ and R$^8$ each represent a fluorine atom, n is greater than/equal to 1 and m is greater than/equal to 0, and the sum of n and m representing an integer from 5 to 15, and X represents a single bond or the group —N(CH$_3$)O$_2$S—.

PROCESS VARIANTS A AND C

According to processes A and C, an ylidene-β-keto ester of the general formula II or VI

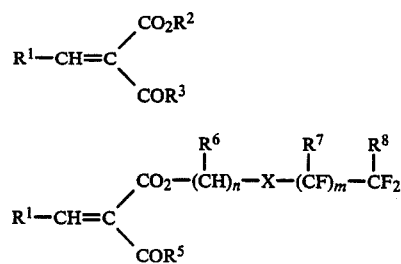

is reacted with an enaminocarboxylic acid ester of the general formula III or formula VII

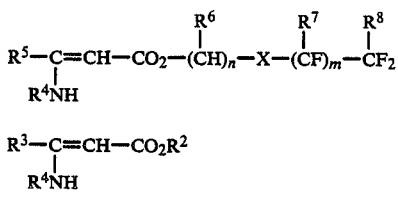

The ylidene-β-keto esters of the general formula II or VI used as starting substances are known from the literature or can be prepared by methods which are known from the literature (compare, for example, G. Jones "The Knoevenagel Condensation" in Org. Reactions, Volume XV, 204 et seq. (1969)).

Examples which may be mentioned are:
Methyl benzylideneformylacetate,
methyl benzylideneacetoacetate,
ethyl 2'-nitrobenzylideneacetoacetate,
n-butyl 3'-nitrobenzylideneacetoacetate,
isobutyl 3'-nitrobenzylideneacetoacetate,
dodecyl 3'-nitrobenzylideneacetoacetate,
cyclopentyl 3'-nitrobenzylideneacetoacetate,
allyl 2'-chlorobenzylideneacetoacetate,
benzyl 2',3'-dichlorobenzylideneacetoacetate,
2-methoxyethyl 2'-chlorobenzylideneacetoacetate,
2-propoxyethyl 3'-chlorobenzylideneacetoacetate,
2-chloroethyl 3'-cyanobenzylideneacetoacetate,
2,2,2-trifluoroethyl 2'-chlorobenzylideneacetoacetate,
2-cyanoethyl 2'-trifluoromethylbenzylideneacetoacetate,
2-acetoxyethyl 2'-difluoromethoxybenzylideneacetoacetate,
2-phenoxymethyl 3'-methylsulphonylbenzylideneacetoacetate,
2-N-benzyl-N-methylaminoethyl 3'-nitrobenzylideneacetoacetate,
2-(3-pyridyl)-ethyl 3'-nitrobenzylideneacetoacetate,
propyl 3'-nitrobenzylidenepropionylacetate,
methyl 4-acetoxy-2-(3'-nitrobenzylidene)-acetoacetate,
ethyl 4-(2-phthalimidoethoxy)-2-(2'-chlorobenzylidene)-acetoacetate,
2-perfluorobutyl-ethyl 3'-nitrobenzylideneacetoacetate,
2-perfluorohexyl-ethyl 3'-chlorobenzylideneacetoacetate,
3-perfluorohexyl-propyl 2'-nitrobenzylideneacetoacetate,
9,9,9-trifluorononyl 2'-cyanobenzylideneacetoacetate,
perfluorohexyl-methyl 2'-trifluoromethylbenzylideneacetoacetate,
2-perfluorobutyl-ethyl 2',3'-dichlorobenzylideneacetoacetate,
3-perfluorohexyl-propyl 2'-chloro-3'-nitrobenzylideneacetoacetate,
perfluorohexylmethyl α-acetyl-β-(pyrid-3-yl)-acrylate,
3-perfluorohexylpropyl α-acetyl-β-(pyrid-2-yl)-acrylate and
2-perfluorobutyl-ethyl α-acetyl-β-(benzoxadiazol-4-yl)-acrylate.

The enaminocarboxylic acid esters of the general formula III or VII used as starting substances are known from the literature or can be prepared by methods which are known from the literature (compare, for example, A.C. Cope, J. Am. Chem. Soc. 67, 1017 (1945)).

Examples which may be mentioned are: Methyl 3-aminocrotonate, butyl 3-aminocrotonate, heptyl 3-aminocrotonate, propyl 3-aminocrotonate, pentyl 3-aminocrotonate, cyclopentyl 3-aminocrotonate, 3,2,2-trifluoroethyl 3-aminocrotonate, 2-cyanoethyl 3-aminocrotonate, 2-acetoxyethyl 3-aminocrotonate, 2-propoxyethyl 3-aminocrotonate, 2-phenoxyethyl 3-aminocrotonate, benzyl 3-aminocrotonate, 2-dimethylaminoethyl 3-aminocrotonate, 2-(N-benzyl-N-methyl)-aminoethyl 3-aminocrotonate, 9,9,9 trifluorononyl 3-aminocrotonate, 3-perfluorohexylpropyl 3-aminocrotonate, perfluorohexylmethyl 3-aminocrotonate and 2-perfluorobutylethyl 3-aminocrotonate.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, and glacial acetic acid, dimethylformamide, dimethylsulphoxide, acetonitrile, pyridine and hexamethylphosphoric acid triamide.

The reaction temperatures can be varied within a substantial range. The reaction is in general carried out between 20° and 150° C., preferably between 20° and 100° C. and in particular at the boiling point of the particular solvent.

The reaction can be carried out under normal pressure, but also under increased pressure. It is in general carried out under normal pressure.

In carrying out the process according to the invention, one mol of the ylidene-β-keto ester of the formula II or VI is reacted with one mol of enaminocarboxylic acid ester of the formula III or VII in a suitable solvent. The substances according to the invention are preferably isolated and purified by a procedure in which the solvent is distilled off in vacuo and the residue, first obtained in the crystalline state by cooling with ice, if necessary, is recrystallized from a suitable solvent.

PROCESS VARIANTS B AND D

According to processes B and D, an ylidene-$\beta$-keto ester of the general formula II or VI

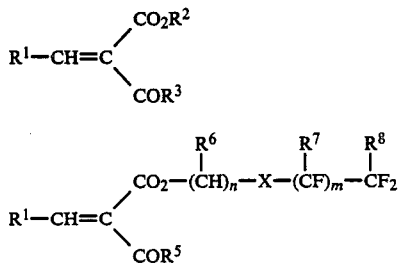

is reacted with a $\beta$-ketocarboxylic acid ester of the general formula IV or VIII

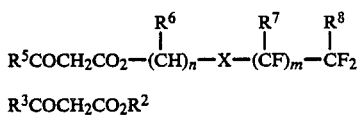

and an amine of the general formula V $$R^4-NH_2 \quad V$$

Examples of the ylidene-$\beta$-keto esters of the formula II or VI used as starting components have already been listed under process variants A and C.

The $\beta$-ketocarboxylic acid esters of the formula IV or VIII used as starting substances are known from the literature or can be prepared by methods which are known from the literature (compare, for example, D. Borrmann, "Umsetzung von Diketen mit Alkoholen, Phenolen und Mercaptanen" ["Reaction of diketene with alcohols, phenols and mercaptans"], in Houben-Weyl, Methoden der Organischen Chemie [Methods of Organic Chemistry], Volume VII/4, 230 et seq. (1968); and Y. Oikawa, K. Sugano and O. Yonemitsu, J. Org. Chem. 43, 2087 (1978)).

Examples which may be mentioned are: Methyl acetoacetate, heptyl acetoacetate, propyl acetoacetate, neopentyl acetoacetate, cyclopentyl acetoacetate, 2-methoxyethyl acetoacetate, 2,2,2-trifluoroethyl acetoacetate, 2-cyanoethyl acetoacetate, 2-acetoxyethyl acetoacetate, benzyl acetoacetate, 2-phenoxyethyl acetoacetate, 2-N-benzyl-N-methyl-aminoethyl acetoacetate, 9,9,9-trifluorononyl acetoacetate, 3-perfluorohexyl-propyl acetoacetate and 2-perfluorobutyl-ethyl acetoacetate.

The amines of the formula V which can be used according to the invention are already known.

Examples which may be mentioned are: Ammonia, methylamine, n-propylamine, $\beta$-methoxyethylamine, benzylamine and 2-(N-morpholino)-ethylamine.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a substantial range. The reaction is in general carried out between 20° and 150° C., but preferably at the boiling point of the particular solvent.

The reaction can be carried out under normal pressure, but also under increased pressure. It is in general carried out under normal pressure.

In carrying out the processes according to the invention, the substances of the formulae II or VI, IV or VIII and V participating in the reaction are each employed in molar amounts. The amine used is advantageously added in an excess of 1 to 2 mols. The compounds according to the invention can easily be purified by recrystallization from a suitable solvent.

PROCESS VARIANTS E AND F

According to processes E and F, an aldehyde of the general formula IX

is reacted either (process E) with an enaminocarboxylic acid ester of the formula III and a $\beta$-ketocarboxylic acid ester of the formula VIII

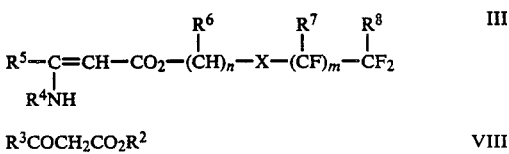

or (process F) with an enaminocarboxylic acid ester of the formula VII

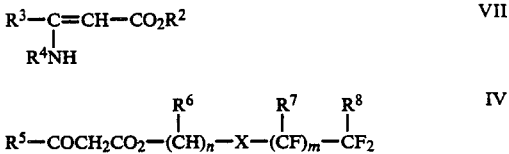

and a $\beta$-ketocarboxylic acid ester of the general formula IV.

The enaminocarboxylic acid esters of the general formula III and VII which can be used according to the invention has already been described under process variants A and C. The $\beta$-ketocarboxylic acid esters of the general formula VIII and IV which can be used according to the invention have already been described under process variants B and D.

The aldehydes of the formula IX which can be used as starting substances are known from the literature or can be prepred by methods which are known from the literature (compare, for example, E. Mosettig, Org. Reactions VIII, 218 et seq. (1954)).

Examples which may be mentioned are: Benzaldehyde, 2- or 3-phenylbenzaldehyde, 2-methylbenzaldehyde, 2- or 3-isopropylbenzaldehyde, 2- or 3-cyclopropylbenzaldehyde, 2,3-tetramethylenebenzaldehyde, 3,4-dioxymethylenebenzaldehyde, 3-methoxybenzaldehyde, 2,- 3- or 4-chloro/bromo/fluorobenzaldehyde, 2- or 3-trifluoromethylbenzaldehyde, 2-, 3- or 4-trifluoromethoxybenzaldehyde, 2-difluoromethoxybenzaldehyde, 2- or 3-nitrobenzaldehyde, 2- or 3-cyanobenzaldehyde, 3-azidobenzaldehyde, 2- or 3-methylthiobenzaldehyde, 3-methylsulphinylbenzaldehyde, 2-methylsulphonylbenzaldehyde, 2,3-dichlorobenzaldehyde, 2-fluoro-3-chlorobenzaldehyde, 2-chloro-3-trifluoromethylbenzaldehyde, 3-chloro-2-trifluoromethylbenzaldehyde, 2,4-dinitrobenzaldehyde, 2-chloro-6-nitrobenzaldehyde, 4-chloro-2-nitrobenzaldehyde, thiophene-2-aldehyde, furan-2-aldehyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2- or -3-aldehyde, 6-methylpyridine-2-aldehyde, 2-methylthio-pyridine-3-aldehyde, indole-3-aldehyde, benzimidazole-2-aldehyde, benzoxazole-4-aldehyde, benzoxadiazole-4-aldehyde, quinoline-4-aldehyde, quinazoline-2-aldehyde and quinoxaline-5-aldehyde.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a substantial range. The reaction is in general carried out between 20° and 150° C., but preferably at the boiling point of the particular solvent.

The reaction can be carried out under normal pressure, but also under increased pressure. It is in general carried out under normal pressure.

In carrying out the process according to the invention, the substances which participate in the reaction are in each case employed in molar amounts.

PROCESS VARIANT G

According to process G, a racemic or enantiomerically pure 1,4-dihydropyridinemonocarboxylic acid of the general formula X or XI

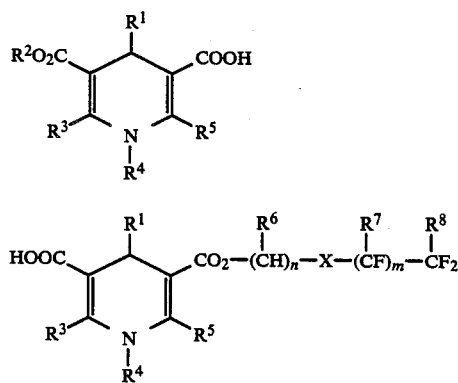

is esterified with an alcohol of the general formula XII or XIII

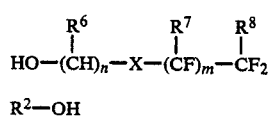

$R^2$—OH  XIII

The racemic or enantiomerically pure 1,4-dihydropyridinemonocarboxylic acids of the general formula X which can be used according to the invention are known from the literature or can be prepared by methods which are known from the literature (compare, for example, DOS (German Published Specification) No. 2,921,429; and T. Shibanuma, M. Iwanami, K. Okuda, T. Takenaka and M. Murakami, Chem. Pharm. Bull. 28, 2809 (1980)).

Examples which may be mentioned are:
1,4-Dihydro-2,6-dimethyl-4-(3-nitrophenyl)-pyridine-3,5-dicarboxylic acid monomethyl ester,
1,4-dihydro-2,6-dimethyl-4-(3-nitrophenyl)-pyridine-3,5-dicarboxylic acid monoisopropyl ester,
1,4-dihydro-2,6-dimethyl-4-(2-nitrophenyl)-pyridine-3,5-dicarboxylic acid monoisobutyl ester,
1,4-dihydro-2,6-dimethyl-4-(2-chlorophenyl)-pyridine-3,5-dicarboxylic acid monomethyl ester,
1,4-dihydro-2,6-dimethyl-4-(2,3-dichlorophenyl)-pyridine-3,5-dicarboxylic acid monomethyl ester,
1,4-dihydro-26-dimethyl-4-(2-trifluoromethylphenyl)-pyridine-3,5-dicarboxylic acid monoethyl ester,
1,4-dihydro-2,6-dimethyl-4-(2,1,3-benzoxadiazol-4-yl)-pyridine-3,5-dicarboxylic acid monoisopropyl ester,
1,4-dihydro-2,6-dimethyl-4-(3-nitrophenyl)-pyridine-3,5-dicarboxylic acid mono-(2-perfluorobutyl-ethyl) ester,
1,4-dihydro-2,6-dimethyl-4-(3-nitrophenyl)-pyridine-3,5-dicarboxylic acid mono-(2-perfluorohexyl-ethyl) ester,
1,4-dihydro-2,6-dimethyl-4-(3-nitrophenyl)-pyridine-3,5-dicarboxylic acid mono-(3-perfluorohexyl-propyl) ester and
1,4-dihydro-2,6-dimethyl-4-(3-nitrophenyl)-pyridine-3,5-dicarboxylic acid mono-(9,9,9-trifluorononyl) ester.

The alcohols which can be used according to the invention are known from the literature or can be prepared by methods which are known from the literature (compare, for example, N. O. Brace, L. W. Marshall, C. J. Pinson and G. van Wingerden, J. Org. Chem. 49, 2361 (1984)).

Examples which may be mentioned are: Methanol, ethanol, butanol, isopropanol, benzyl alcohol, 2-methoxyethanol, 2-dimethylaminoethanol, 2-(N-benzyl-N-methyl)-aminoethanol, 2-perfluorobutylethanol, perfluorohexylmethanol, 3-perfluorohexylpropanol and 9,9,9-trifluorononanol.

The procedure of the process according to the invention is based on the method known from the literature for esterification of carboxylic acids. The carboxylic acid is thereby initially converted into an activated form, such as, for example, the acid chloride or the imidazolide, which is either isolated as such and reacted in a second reaction step, or is alkanolized in situ directly to give the compounds according to the invention. Examples of activating agents which may be mentioned are, in addition to the inorganic halides, such as thionyl chloride, phosphorus trichloride or phosphorus pentachloride, or carbonyldiimidazole, carbodiimides, such as dicyclohexylcarbodiimide or 1-cyclohexyl-3-[2-(N-methyl-morpholino)-ethyl]-carbodiimide p-toluenesulphonate or N-hydroxyphthalimide or N-hydroxybenzotriazole in the presence of dicyclohexylcarbodiimide. The 1,4-dihydropyridinemonocarboxylic acids can of course also be converted into salts, which can be reacted with substrates of the general formula XIV or XV

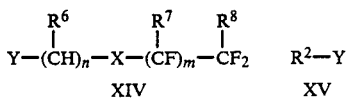

in which

Y represents a nucleofugic group, such as, for example, iodide or tosylate, to give the compounds according to the invention.

Possible diluents are all the inert organic solvents. These include, preferably, ethers, such as dioxane, tetrahydrofuran, glycol monomethyl ether or glycol dimethyl ether, halogenated hydrocarbons, such as methylene chloride or chloroform, dimethylformamide, dimethylsulphoxide, acetonitrile, pyridine and hexamethylphosphoric acid triamide. If the activated intermediate stages of the 1,4-dihydropyridinemonocarboxylic acids are isolated, the alcohols of the formula XII or XIII can also be used by themselves as the diluent.

The alkanolysis is advantageously accelerated by addition of catalytic or molar amounts of a basic auxiliary.

The reaction temperatures can be varied within a substantial range. The reaction is in general carried out between 20° and 150° C., but preferably at the boiling point of the particular solvent.

The reaction can be carried out under normal pressure, but also under increased pressure. It is in general carried out under normal pressure.

PROCESS VARIANT H

In the case where $R^3$ or $R^5$ in the general formula I represents a formyl group, these compounds according to the invention are preferably prepared by acid hydrolysis of the compounds of the general formula I according to the invention in which $R^3$ or $R^5$ denotes a dialkoxymethyl radical with 1 or 2 carbon atoms per alkoxy group.

If $R^3$ or $R^5$ in the general formula I represents a nitrile group, these compounds are preferably obtained by reacting the compounds of the general formula I according to the invention in which $R^3$ or $R^5$ represents a formyl group with hydroxylamine and subsequently dehydrating the resulting oxime, for example by heating in a mixture of acetic anhydride and glacial acetic acid.

If $R^3$ or $R^5$ in the general formula I represents an alkyl radical which is substituted by a hydroxyl group, these substances are obtained by hydrolysis of the corresponding acetoxy derivatives according to the invention under acid or alkaline conditions.

In the case where $R^3$ or $R^5$ in the general formula I represents an alkyl radical which is substituted by an amino or an aminoalkoxy group, these substances according to the invention are prepared, for example by reacting the corresponding phthalimido or phthalimidoalkoxy compounds according to the invention with hydrazine in accordance with the prior art.

The above preparation processes are given merely for illustration, and the preparation of the compounds of the formula I is not limited to these processes, but any modification of these processes can be applied in the same manner to the preparation of the compounds according to the invention.

The new compounds have a broad and diverse pharmacological action spectrum.

In detail, it has been possible to demonstrate the following main actions in animal experiments:

1. On parenteral, oral and perlingual administration, the compounds effect a clear and long-lasting dilation of the coronary vessels. This action on the coronary vessels is intensified by a simultaneous nitrite-like effect of reducing the load on the heart. They influence or modify cardiac metabolism in the sense of a saving of energy.
2. The excitability of the stimulus conduction and excitation conduction system within the heart is reduced, so that an antifibrillation action detectable in therapeutic doses results.
3. The tone of the smooth muscle of the vessels is greatly reduced under the action of the compounds. This vasospasmolytic action can take place in the entire vascular system or can manifest itself more or less isolated in circumscribed vascular regions.
4. The compounds having a long-lasting effect of reducing the blood pressure of normotensive and hypertensive animals and can thus be used as antihypertensive agents.
5. The compounds have powerful muscular spasmolytic actions which manifest themselves on the smooth muscle of the stomach, intestinal tract, urogenital tract and respiratory system.

On the basis of these properties, the compounds according to the invention are particularly suitable for the prophylaxis and therapy of acute and chronic ischaemic cardiac diseases in the broadest sense, for the therapy of high blood pressure and for the treatment of disturbances in cerebral and peripheral circulation.

The new active compounds can be converted in a known manner into the customary formulations, as tablets, capsules, dragees, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which are sufficient to achieve the dosage range stated.

The formulations are prepared, for example by extending the active compounds with solvents and/or excipients, if appropriate using emulsifying agents and/or dispersing agents, and, for example in the case of the use of water as a diluent, organic solvents can be used, if appropriate, as auxiliary solvents.

Examples of auxiliaries which may be mentioned are: Water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol) solid excipients, such as, for example, natural rock powders, for example kaolins, aluminas, talc and chalk), synthetic rock powders (for example highly disperse silicic acid and silicates) and sugars (for example sucrose, lactose and glucose), emulsifying agents (for example polyoxyethylene fatty acid esters), polyoxyethylene fatty alcohol ethers (for example lignin, sulphite waste liquors, methylcellulose, starch and polyvinylpyrrolidone) and lubricants (for example magnesium stearate, talc, stearic acid and sodium sulphate).

Administration is carried out in the customary manner, preferably orally or parenterally, in particular perlingually or intravenously. In the case of oral use, tab-

PREPARATION EXAMPLES

Example 1 (Process variant A)

Methyl 4-perfluoroethyl-butyl 1,4-dihydro-2,6-dimethyl-4-(3-nitrophenyl)-pyridine-3,5-dicarboxylate

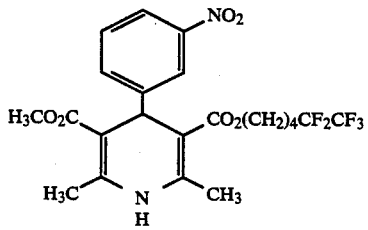

8.69 g (35 mmol) of methyl 2-(3-nitrobenzylidene)acetoacetate were taken up in 150 ml of isopropanol together with 9.63 g (35 mmol) of 4-perfluoroethyl-butyl 3-aminocrotonate and the mixture was heated under reflux for 15 hours. The solvent was then distilled off under reduced pressure and the oily residue was made to crystallize by trituration with a little ether. The crude product was filtered off with suction and recrystallized from ethanol.

Melting point: 119°–121° C.
Yield: 13.3 g (75% of theory).

Example 2 (Process variant C)

Methyl 2-perfluorobutyl-ethyl 1,4-dihydro-2,6-dimethyl-4-(3-nitrophenyl)-pyridine-3,5-dicarboxylate

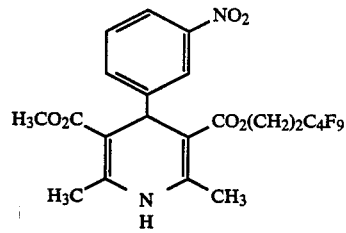

A solution of 33.69 g (79 mmol) of 2-perfluorobutyl-ethyl 2-(3-nitrobenzylidene)-acetoacetate and 8.06 g (70 mmol) of methyl 3-aminocrotonate in 200 ml of ethanol was heated at the boiling point for 15 hours. The solvent was then distilled off in vacuo and the solid residue was purified by column chromatography over silica gel with a mixture of toluene/acetone=5/1 as the eluting agent.

Melting point: 106° C.
Yield: 28.7 g (71% of theory).

Example 3 (Process variant G)

Isopropyl 4-perfluoroethyl-butyl 1,4-dihydro-2,6-dimethyl-4-(3-nitrophenyl)-pyridine-3,5-dicarboxylate

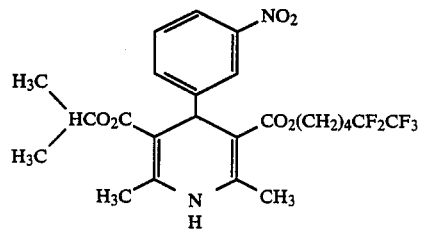

(a) 10 g (62 mmol) of 1,1'-carbonyldiimidazole were added to a solution of 18 g (50 mmol) of racemic 1,4-dihydro-2,6-dimethyl-4-(3-nitrophenyl)-pyridine-3,5-dicarboxylic acid monoisopropyl ester in 125 ml of absolute tetrahydrofuran. The mixture was stirred at room temperature for 45 minutes and then heated at the boiling point for 45 minutes. After cooling, the solvent was distilled off in vacuo, the residue was taken up in methylene chloride and the mixture was washed with dilute sodium hydroxide solution and water. The organic phase was dried over anhydrous sodium sulphate and concentrated under reduced pressure. The oily residue rapidly crystallized completely on trituration with ether and it was filtered off with suction and washed with ether. After drying in vacuo, 19 g (93% of theory) of racemic 1,4-dihydro-2,6-dimethyl-4-(3-nitrophenyl)-pyridine-3,5-dicarboxylic acid isopropyl ester-imidazolide of melting point 190°–192° C. resulted.

(b) 5.13 g (12.5 mmol) of the racemic 1,4-dihydro-2,6-dimethyl-4-(3-nitrophenyl)-pyridine-3,5-dicarboxylic acid isopropyl ester-imidazol prepared above were taken up in 50 ml of absolute tetrahydrofuran together with 4.80 g (25 mmol) of 4-perfluoroethyl-butan-1-ol, and, after addition of a spatula-tip of sodium hydride, the mixture was heated under reflux for 1 hour. After cooling, the solvent was distilled off in vacuo and the residue was purified over silica gel with methylene chloride/methanol=10/1 as the eluting agent. 4.5 g (67% of theory) of racemic isopropyl 4-perfluoroethyl-butyl 1,4-dihydro-2,6-dimethyl-4-(3-nitrophenyl)-pyridine-3,5-dicarboxylate were obtained as a highly viscous oil (M+=532), N (calculated) 5.24%, N (found) 4.9%.

Example 4

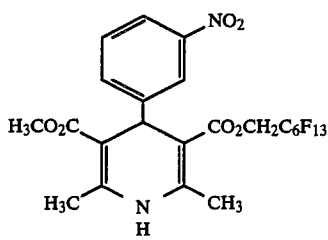

Methyl perfluorohexylmethyl 1,4-dihydro-2,6-dimethyl-4-(3-nitrophenyl)-pyridine-3,5-dicarboxylate of melting point: 114° C. (toluene) was obtained analogously to Example 1 by reaction of methyl 2-(3-nitrobenzylidene)acetoacetate with perfluorohexylmethyl 3-aminocrotonate in ethanol.

Yield: 67% of theory.

Example 5

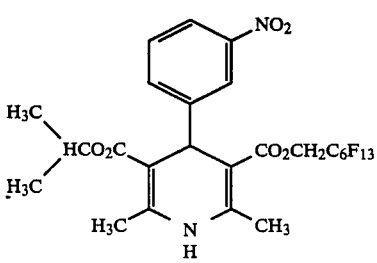

Isopropyl perfluorohexylmethyl 1,4-dihydro-2,6-dimethyl-4-(3-nitrophenyl)-pyridine-3,5-dicarboxylate of melting point: 116° C. (ether/petroleum ether) was obtained analogously to Example 3 by reaction of 1,4-dihydro-2,6-dimethyl-4-(3-nitrophenyl)-pyridine-3,5-dicarboxylic acid monoisopropyl ester with carbonyldiimidazole and subsequent alkanolysis of the imidazolide with perfluorohexylmethanol in tetrahydrofuran.

Yield: 63% of theory.

Example 6

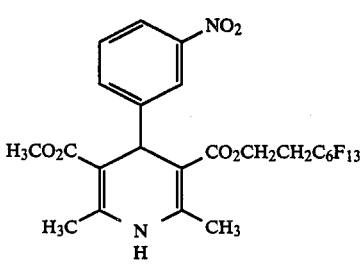

Methyl 2-perfluorohexyl-ethyl 1,4-dihydro-2,6-dimethyl-4-(3-nitrophenyl)-pyridine-3,5-dicarboxylate of melting point: 114° C. was obtained analogously to Example 1 by reaction of methyl 2-(3-nitrobenzylidene)-acetoacetate with 2-perfluorohexyl-ethyl 3-aminocrotonate in isopropanol.

Yield: 61% of theory.

Example 7

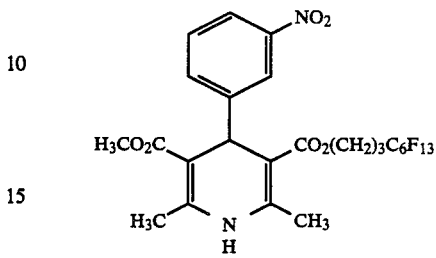

Methyl 3-perfluorohexyl-propyl, 1,4-dihydro-2,6-dimethyl-4-(3-nitrophenyl)-pyridine-3,5-dicarboxylate of melting point: 146° C. (ethanol) was obtained analogously to Example 1 by reaction of methyl 2-(3-nitrobenzylidene)acetoacetate with 3-perfluorohexyl-propyl 3-aminocrotonate in isopropanol.

Yield: 63% of theory.

Example 8 (Process variant G)

Methyl 3-perfluorohexyl-propyl (−)-1,4-dihydro-2,6-dimethyl-4-(3-nitrophenyl)-pyridine-3,5-dicarboxylate

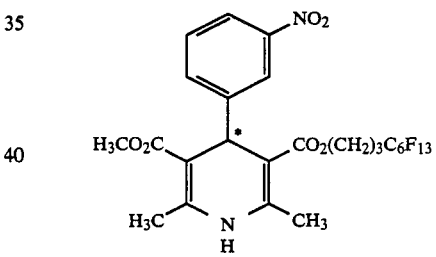

12.9 g (79.5 mmol) of 1,1'-carbonyldiimidazole were added in portions to a suspension of 21.2 g (63.8 mmol) of dextrorotatory, enantiomerically pure 1,4-dihydro-2,6-dimethyl-4-(3-nitrophenyl)-pyridine-3,5-dicarboxylic acid monomethyl ester in 200 ml of absolute tetrahydrofuran at the boiling point. After the reaction mixture had been stirred under reflux for 1 hour, 36.15 g (95.7 mmol) of 3-perfluorohexylpropan-1-ol and a spatula-tip of sodium hydride were added and the mixture was heated at the boiling point for a further 2 hours. The solvent was then distilled off under reduced pressure and the residue was purified by column chromatography over silica gel with a mixture of methylene chloride/methanol=10/1 as the eluting agent. The crude product was extracted by stirring in four times the amount of ether/petroleum ether=1/1 and was filtered off with suction and dried in vacuo.

Melting point: 133°–134° C.

Yield: 34.7 g (79% of theory)

$[\alpha]_D^{20} = -17.52°$ (c=0.626% w/v, ethanol).

Example 9 (Process variant G)

Methyl 3-perfluorohexyl-propyl (+)-1,4-dihydro-2,6-dimethyl-4-(3-nitrophenyl)-pyridine-3,5-dicarboxylate

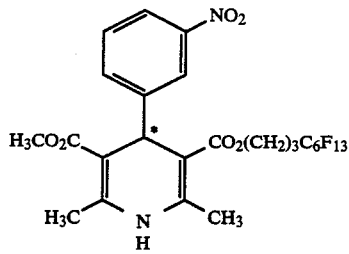

(a) 18.32 g (113 mmol) of 1,1'-carbonyldiimidazole were introduced in portions into a suspension of 30.1 g (90.6 mmol) of laevorotatory, enantiomerically pure 1,4-dihydro-2,6-dimethyl-4-(3-nitrophenyl)-pyridine-3,5-dicarboxylic acid monomethyl ester in 200 ml of absolute tetrahydrofuran at the boiling point, while stirring. The mixture was heated under reflux for 1 hour and, after cooling, was thoroughly mixed vigorously with 400 ml of water and 40 ml of saturated sodium bicarbonate solution. The product which had precipitated was filtered off with suction, washed with water and dried in vacuo at 60° C. 28.2 g (81% of theory) of dextrorotatory, enantiomerically pure 1,4-dihydro-2,6-dimethyl-4-(3-nitrophenyl)-pyridine-3,5-carboxylic acid methyl ester-imidazolide of melting point: 198° C. resulted.

$[\alpha]_D^{20} = +166.23°$ (c=0.533% w/v, ethanol).

(b) A mixture of 9.7 g (25.4 mmol of the dextrorotatory 1,4-dihydro-2,6-dimethyl-4-(3-nitrophenyl)-pyridine-3,5-dicarboxylic acid methyl ester-imidazolide prepared above and 19.03 g (50.8 mmol) of 3-perfluorohexyl-propan-1-ol in 100 ml of absolute tetrahydrofuran was heated under reflux for 1 hour, after addition of 2 spatula-tips of sodium hydride. The solvent was then distilled off in vacuo and the residue was purified by column chromatography over silica gel using a mixture of methylene chloride/methanol=1/1 as the eluting agent. The crude product was extracted by stirring in four times the amount of ether/petroleum ether=1/1, and was filtered off with suction and dried in vacuo. 14.1 g (80% of theory) of dextrorotatory, enantiomerically pure methyl 3-perfluorohexyl-propyl 1,4-dihydro-2,6-dimethyl-4-(3-nitrophenyl)-pyridine-3,5-dicarboxylate of melting point: 133°-134° C. resulted.

$[\alpha]_D^{20} = +17.48°$ (c=0.976% w/v, ethanol).

Example 10

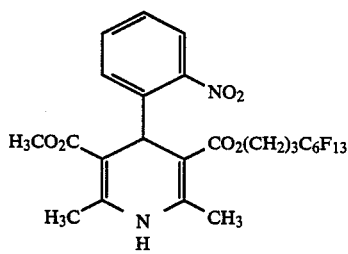

Methyl 3-perfluorohexyl-propyl 1,4-dihydro-2,6-dimethyl-4-(2-nitrophenyl)-pyridine-3,5-dicarboxylate of melting point: 98° C. (ether/petroleum ether) was obtained analogously to Example 1 by reaction of methyl 2-(2-nitrobenzylidene)-acetoacetate with 3-perfluorohexyl-propyl 3-aminocrotonate in isopropanol.

Yield: 53% of theory.

Example 11

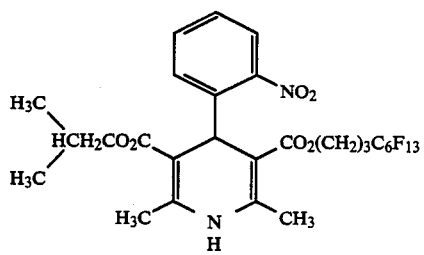

Isobutyl 3-perfluorohexyl-propyl 1,4-dihydro-2,6-dimethyl-4-(2-nitrophenyl)-pyridine-3,5-dicarboxylate was obtained as a highly viscous oil (M+ =734) analogously to Example 1 by reaction of isobutyl 2-(2-nitrobenzylidene)-acetoacetate with 3-perfluorohexyl-propyl 3-aminocrotonate.

Yield: 49% of theory
C (calculated) 44.9% C (found) 45.1%.

Example 12

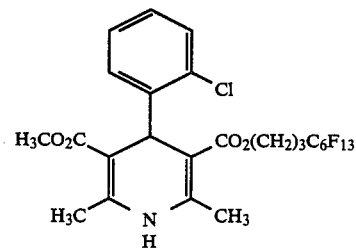

Methyl 3-perfluorohexyl-propyl 1,4-dihydro-2,6-dimethyl-4-(2-chlorophenyl)-pyridine-3,5-dicarboxylate of melting point: 107° C. (toluene) was obtained analogously to Example 1 by reaction of methyl 2-(2-chlorobenzylidene)-acetoacetate with 3-perfluorohexyl-propyl 3-aminocrotonate in methanol.

Yield: 52% of theory.

Example 13

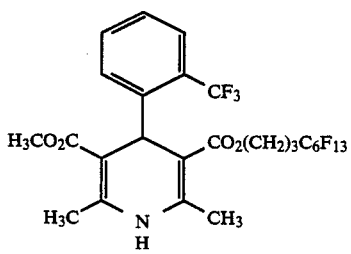

Methyl 3-perfluorohexyl-propyl 1,4-dihydro-2,6-dimethyl-4-(2-trifluoromethylphenyl)-pyridine-3,5-dicarboxylate of melting point: 110° C. (ether/petroleum ether) was obtained analogously to Example 1 by reaction of methyl 2-(2-trifluoromethylbenzylidene)- acetoacetate with 3-perfluorohexyl-propyl 3-aminocrotonate in isopropanol.
Yield: 46% of theory.

Example 14

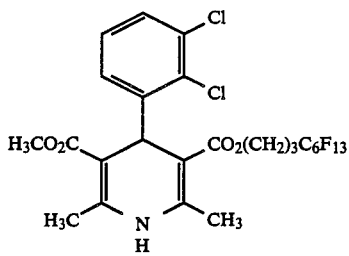

Methyl 3-perfluorohexyl-propyl 1,4-dihydro-2,6-dimethyl-4-(2,3-dichlorophenyl)-pyridine-3,5-dicarboxylate of melting point: 100° C. (petroleum ether) was obtained analogously to Example 1 by reaction of methyl 2-(2,3-dichlorobenzylidene)-acetoacetate with 3-perfluorohexylpropyl 3-aminocrotonate in ethanol.
Yield: 50% of theory.

Example 15

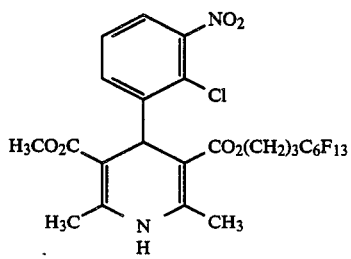

Methyl 3-perfluorohexyl-propyl 1,4-dihydro-2,6-dimethyl-4-(2-chloro-3-nitrophenyl)-pyridine-3,5-dicarboxylate was obtained as a yellow oil (M+ =726) analogously to Example 1 by reaction of methyl 2-(2-chloro-3-nitrobenzylidene)-acetoacetate with 3-perfluorohexyl-propyl 3-aminocrotonate in ethanol.
Yield: 53% of theory.

Example 16

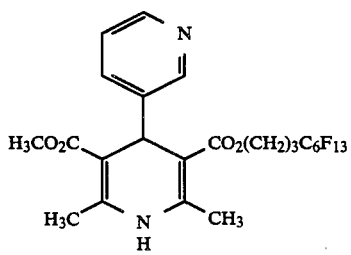

Methyl 3-perfluorohexyl-propyl 1,4-dihydro-2,6-dimethyl-4-(pyrid-3-yl)-pyridine-3,5-dicarboxylate of melting point: 155° C. (ether) was obtained analogously to Example 1 by reaction of methyl 2-acetyl-3-(pyrid-3-yl)acrylate with 3-perfluorohexyl-propyl 3-aminocrotonate.
Yield: 57% of theory.

Example 17

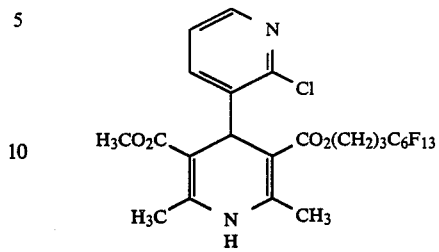

Methyl 3-perfluorohexyl-propyl 1,4-dihydro-2,6-dimethyl-4-(2-chloro-pyrid-3-yl)-pyridine-3,5-dicarboxylate of melting point: 155° C. was obtained analogously to Example 1 by reaction of methyl 2-acetyl-3-(2chloro-pyrid-3-yl)-acrylate with 3-perfluorohexyl-propyl 3-aminocrotonate in isopropanol.
Yield: 48% of theory.

Example 18

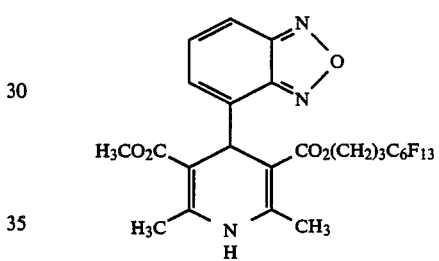

Methyl 3-perfluorohexyl-propyl 1,4-dihydro-2,6-dimethyl-4-(2,1,3-benzoxadiazol-4-yl)-pyridine-3,5-dicarboxylate of melting point: 110° C. (ether) was obtained analogously to Example 1 by reaction of methyl 2-acetyl-3-(2,1,3-benzoxadiazol-4-yl)-acrylate with 3-perfluorohexyl-propyl 3-aminocrotonate in propanol.
Yield: 43% of theory.

Example 19

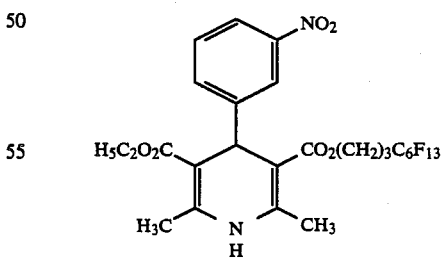

Ethyl 3-perfluorohexyl-propyl 1,4-dihydro-2,6-dimethyl-4-(3-nitrophenyl)-pyridine-3,5-dicarboxylate of melting point 119° C. (ethanol) was obtained analogously to Example 1 by reaction of ethyl 2-(3-nitrobenzylidene)acetoacetate with 3-perfluorohexyl-propyl 3-aminocrotonate in isopropanol.
Yield: 59% of theory.

Example 20

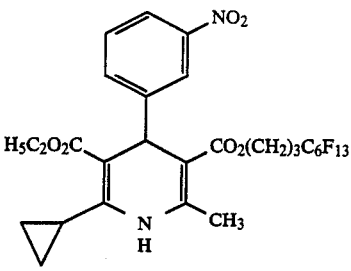

3-ethyl 5-(3-perfluorohexyl-propyl) 1,4-dihydro-2-cyclopropyl-6-methyl-4-(3-nitrophenyl)-pyridine-3,5-dicarboxylate of melting point: 112° C. (ether/petroleum ether) was obtained analogously to Example 1 by reaction of ethyl 2-cyclopropylcarbonyl-3-(3-nitrophenyl)-acrylate with 3-perfluorohexyl-propyl 3-aminocrotonate in isopropanol.

Yield: 42% of theory.

Example 21

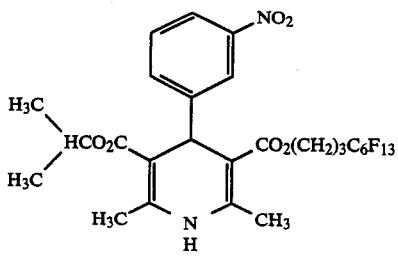

Isopropanol 3-perfluorohexyl-propyl 1,4-dihydro-2,6-dimethyl-4-(3-nitrophenyl)-pyridine-3,5-dicarboxylate of melting point: 109° C. (ethanol) was obtained analogously to Example 1 by reaction of isopropyl 2-(3-nitrobenzylidene)-acetoacetate with 3-perfluorohexyl-propyl 3-aminocrotonate in isopropanol.

Yield: 65% of theory.

Example 22

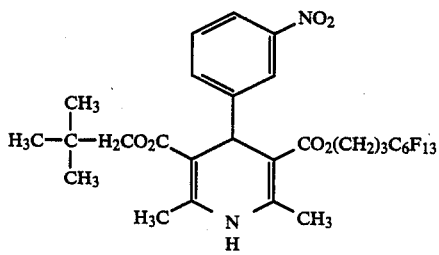

Neopentyl 3-perfluorohexyl-propyl 1,4-dihydro-2,6-dimethyl-4-(3-nitrophenyl)-pyridine-3,5-dicarboxylate of melting point: 130° C. (ether/petroleum ether) was obtained analogously to Example 1 by reaction of neopentyl 2-(3-nitrobenzylidene)-acetoacetate with 3-perfluorohexyl-propyl 3-aminocrotonate in isoproanol.

Yield: 68% of theory.

Example 23

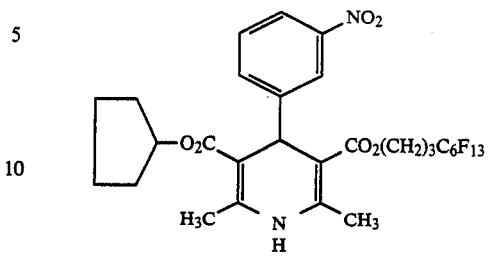

Cyclopentyl 3-perfluorohexyl-propyl 1,4-dihydro-2,6-dimethyl-4-(3-nitrophenyl)-pyridine-3,5-dicarboxylate of melting point: 118° C. (ether/petroleum ether) was obtained analogously to Example 1 by reaction of cyclopentyl 2-(3-nitrobenzylidene)-acetoacetate with 3-perfluorohexyl-propyl 3-aminocrotonate in ethanol.

Yield: 68% of theory.

Example 24

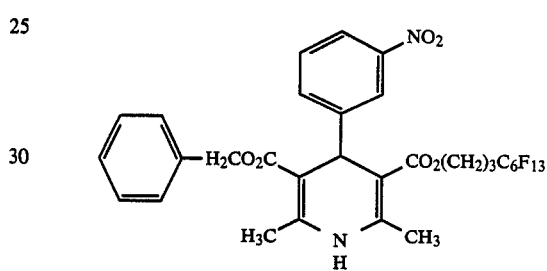

Benzyl 3-perfluorohexyl-propyl 1,4-dihydro-2,6-dimethyl-4-(3-nitrophenyl)-pyridine-3,5-dicarboxylate of melting point: 109° C. (ethanol) was obtained analogously to Example 1 by reaction of benzyl 2-(3-nitrobenzylidene)-acetoacetate with 3-perfluorohexyl-propyl 3-aminocrotonate in isopropanol.

Yield: 71% of theory.

Example 25

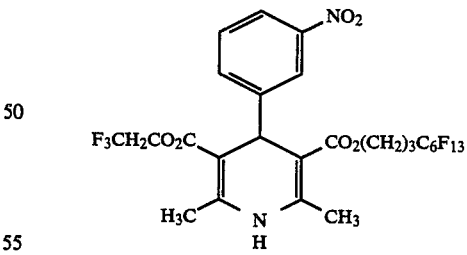

2,2,2-Trifluoroethyl 3-perfluorohexyl-propyl 1,4-dihydro-2,6-dimethyl-4-(3-nitrophenyl)-pyridine-3,5-dicarboxylate of melting point: 137° C. (petroleum ether) was obtained analogously to Example 8 by reaction of racemic 1,4-dihydro-2,6-dimethyl-4-(3-nitrophenyl)-pyridine-3,5-dicarboxylic acid mono-(3-perfluorohexyl-propyl)ester with 1,1'-carbonyldiimidazole in tetrahydrofuran and subsequent alkanolysis of the resulting 1,4-dihydro-2,6-dimethyl-4-(3-nitrophenyl)-pyridine-3,5-dicarboxylate acid 3-perfluorohexyl-propyl)ester-imidazolide with 2,2,2-trifluoroethanol.

Yield: 81% of theory.

Example 26

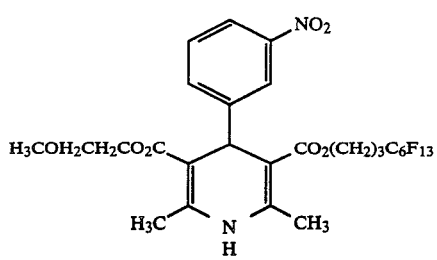

2-Methoxyethyl 3-perfluorohexyl-propyl 1,4-dihydro-2,6-dimethyl-4-(3-nitrophenyl)-pyridine-3,5-dicarboxylate of melting point: 127° C. (ether/petroleum ether) was obtained analogously to Example 1 by reaction of 2-methoxyethyl 2-(3-nitrobenzylidene)-acetoacetate with 3-perfluorohexyl-propyl 3-aminocrotonate in isopropanol.

Yield: 75% of theory.

Example 27

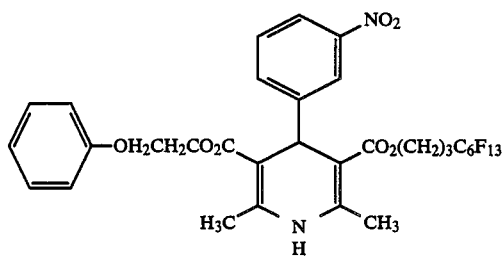

2-Phenoxyethyl 3-perfluorohexyl-propyl 1,4-dihydro-2,6-dimethyl-4-(3-nitrophenyl)-pyridine-3,5-dicarboxylate of melting point: 113° C. (ether/petroleum ether) was obtained analogously to Example 8 by reaction of racemic 1,4-dihydro-2,6-dimethyl-4-(3-nitrophenyl)-pyridine-3,5-dicarboxylic acid mono-(3-perfluorohexyl-propyl)ester with 1,1'-carbonyldiimidazole in tetrahydrofuran and subsequent alkanolysis of the resulting 1,4-dihydro-2,6-dimethyl-4-(3-nitrophenyl)-pyridine-3,5-dicarboxylic acid 3-perfluorohexyl-propyl ester-imidazole with 2-phenoxyethanol.

Yield: 51% of theory.

Example 28

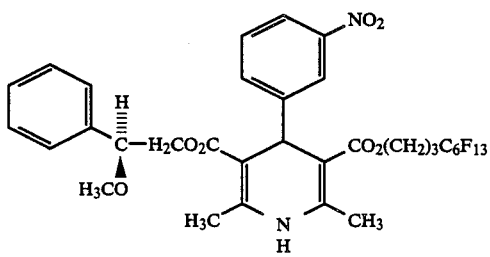

(S)-2-Methoxy-2-phenylethyl 3-perfluorohexyl-propyl 1,4-dihydro-2,6-dimethyl-4-(3-nitrophenyl)-pyridine-3,5-dicarboxylate of melting point: 79° C. (toluene) was obtained analogously to Example 2 by reaction of 3-perfluorohexyl-propyl 2-(3-nitrobenzylidene)-acetoacetate with (S)-2-methoxy-2-phenylethyl 3-aminocrotonate in ethanol.

Yield: 41% of theory.

Example 29

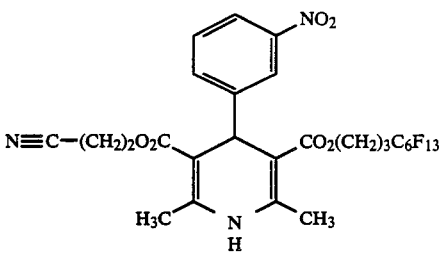

2-Cyanoethyl 3-perfluorohexyl-propyl 1,4-dihydro-2,6-dimethyl-4-(3-nitrophenyl)-pyridine-3,5-dicarboxylate of melting point: 138° C. (ethanol) was obtained analogously to Example 1 by reaction of 2-cyanoethyl 2-(3-nitrobenzylidene)-acetoacetate with 3-perfluorohexyl-propyl 3-aminocrotonate in ethanol.

Yield: 75% of theory.

Example 30 (Process variant G)

2-Dimethylaminoethyl 3-perfluorohexyl-propyl 1,4-dihydro-2,6-dimethyl-4-(3-nitrophenyl)-pyridine-3,5-dicarboxylate

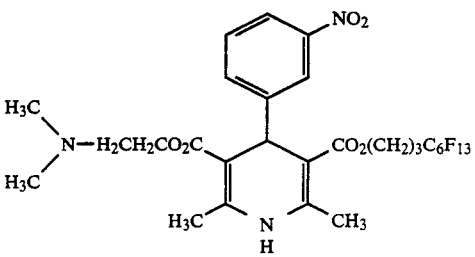

(a) 10.2 g (15 mmol) of 1,4-dihydro-2,6-dimethyl-4-(3-nitrophenyl)-pyridine-3,5-dicarboxylic acid mono-(3-perfluorohexyl-propyl) ester were taken up in 30 ml of absolute tetrahydrofuran and, after addition of 3.65 g (22.5 mmol) of 1,1'-carbonyldiimidazole, the mixture was heated under reflux for 1 hour. After cooling, the reaction solution was thoroughly mixed vigorously with 100 ml of methylene chloride and 50 ml of dilute sodium hydroxide solution and the organic phase was then separated off, washed with water and, after drying over sodium sulphate, concentrated under reduced pressure. The residue was stirred in a mixture of equal parts of ether and petroleum ether, filtered off with suction and dried in vacuo. 7.7 g (71%) of 1,4-dihydro-2,6-dimethyl-4-(3-nitrophenyl)pyridine-3,5-dicarboxylic acid 3-perfluorohexylpropyl ester-imidazolide of melting point: 156° C. resulted.

(b) 7.28 g (10 mmol) of the 1,4-dihydro-2,6-dimethyl-4-(3-nitrophenyl)-pyridine-3,5-dicarboxylic acid 3-perfluorohexyl-propyl ester-imidazolide prepared above were taken up in 50 ml of absolute tetrahydrofuran, together with 1.34 g (15 mmol) of 2-dimethylaminoethanol, and, after addition of a spatula-tip of sodium hydride, the mixture was stirred at room temperature for 1 hour. The solvent was then distilled off under reduced pressure and the residue was purified by column chromatography over silica gel with a mixture of methylene chloride/methanol=10/1 as the eluting agent. The product was stirred in ether/petroleum ether=1/1 and filtered off with suction. After drying, 4.9 g (65%) of 2-dimethylaminoethyl 3-perfluorohexyl-propyl 1,4-dihydro-2,6-dimethyl-4-(3-nitrophenyl)-pyridine-3,5-dicarboxylate of melting point: 98° C. remained.

Example 31

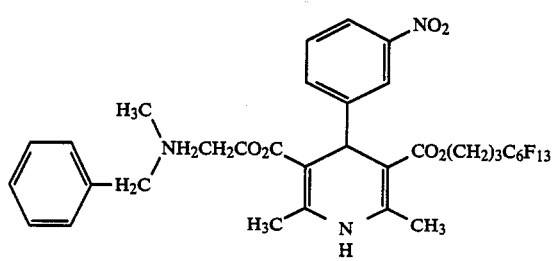

2-(N-Benzyl-N-methyl-amino)-ethyl 3-perfluorohexylpropyl 1,4-dihydro-2,6-dimethyl-4-(3-nitrophenyl)-pyridine-3,5-dicarboxylate of melting point: 96° C. was obtained analogously to Example 30 by alkanolysis of 1,4-dihydro-2,6-dimethyl-4-(3-nitrophenyl)-pyridine-3,5-dicarboxylic acid 3-perfluorohexyl-propyl ester-imidazolide with 2-(N-benzyl-N-methyl-amino)-ethanol in tetrahydrofuran.

Yield: 70% of theory.

Example 32

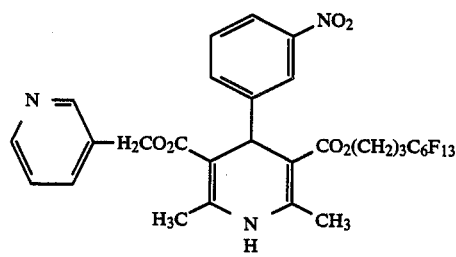

3-Pyridylmethyl 3-perfluorohexyl-propuyl 1,4-dihydro-2,6-dimethyl-4-(3-nitrophenyl)-pyridine-3,5-dicarboxylate of melting point: 155° C. was obtained analogously to Example 30 by alkanolysis of 1,4-dihydro-2,6-dimethyl-4-(3-nitrophenyl)-pyridine-3,5-dicarboxylic acid 3-perfluorohexyl-propyl ester-imidazolide with 3-hydroxymethylpyridine in tetrahyrofuran.

Yield: 55% of theory.

Example 33

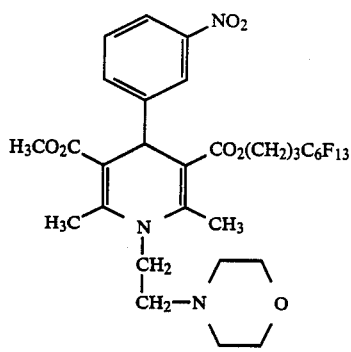

Methyl 3-perfluorohexyl-propyl 1,4-dihydro-2,6-dimethyl-1-(2-N-morpholinoethyl)-4-(3-nitrophenyl)-pyridine-3,5-dicarboxylate of melting point: 70° C. (ether) was obtained analogously to Example 1 by reaction of methyl 2-(3-nitrobenzylidene)-acetoacetate with 3-perfluorohexylpropyl 3-(2-N-morpholinoethylamino)-crotonate in pyridine/glacial acetic acid.

Yield: 39% of theory.

Example 34

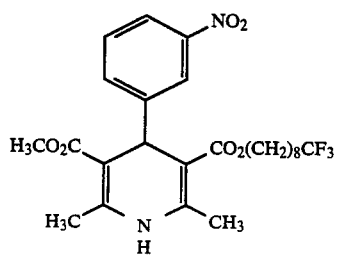

Methyl 9,9,9-trifluorononyl 1,4-dihydro-2,6-dimethyl-4-(3-nitrophenyl)-pyridine-3,5-dicarboxylate of melting point: 136° C. (ethanol) was obtained analogously to Example 1 by reaction of methyl 2-(3-nitrobenzylidene)acetoacetate with 9,9,9-trifluorononyl 3-aminocrotonate in isopropanol.

Yield: 70% of theory.

Example 35

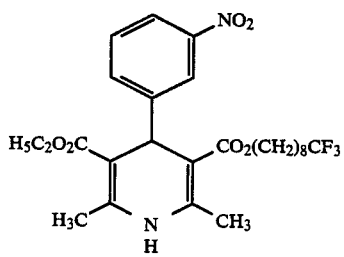

Ethyl 9,9,9-trifluorononyl 1,4-dihydro-2,6-dimethyl-4-(3-nitrophenyl)-pyridine-3,5-dicarboxylate of melting point: 110° C. (ethanol) was obtained analogously to Example 1 by reaction of ethyl 2-(3-nitrobenzylidene)acetoacetate with 9,9,9-trifluorononyl 3-aminocrotonate in ethanol.

Yield: 66% of theory.

Example 36

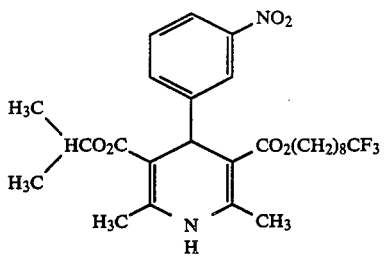

Isopropyl 9,9,9-trifluorononyl 1,4-dihydro-2,6-dimethyl-4-(3-nitrophenyl)-pyridine-3,5-dicarboxylate of melting point: 114° C. (ethanol) was obtained analogously to Example 1 by reaction of isopropyl 2-(3-nitrobenzylidene)-acetoacetate with 9,9,9-trifluorononyl 3-aminocrotonate in isopropanol.

Yield: 61% of theory.

Example 37

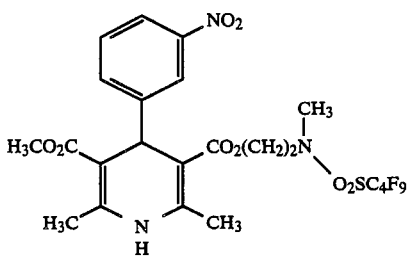

Methyl 2-(N-methyl-N-perfluorobutylsulphonylamino)ethyl, 1,4-dihydro-2,6-dimethyl-4-(3-nitrophenyl)-pyridine-3,5-dicarboxylate of melting point: 115° C. (isopropanol) was obtained analogously to Example 1 by reaction of methyl 2-(3-nitrobenzylidene)-acetoacetate with 2-(N-methyl-N-perfluorobutylsulphonylamino)-ethyl 3-aminocrotonate in isopropanol.

Yield: 39% of theory.

Example 38

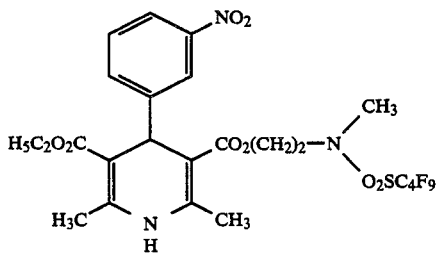

Ethyl 2-(N-methyl-N-perfluorobutylsulphonylamino)ethyl 1,4-dihydro-2,6-dimethyl-4-(3-nitrophenyl)-pyridine-3,5-dicarboxylate of melting point: 55° C. (isopropanol) was obtained analogously to Example 1 by reaction of ethyl 2-(3-nitrobenzylidene)-acetoacetate with 2-(N-methyl-N-perfluorobutylsulphonylamino)-ethyl 3-aminocrotonate in isopropanol.

Yield: 55% of theory.

Example 39

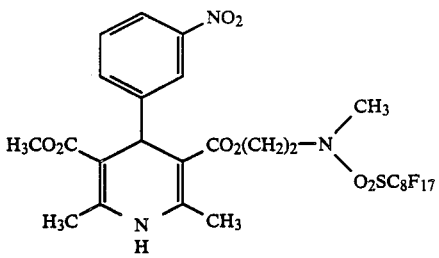

Methyl 2-(N-methyl-N-perfluorooctylsulphonylamino)-ethyl 1,4-dihydro-2,6-dimethyl-4-(3-nitrophenyl)pyridine-3,5-dicarboxylate of melting point: 136° C. (ethyl acetate) was obtained analogously to Example 1 by reaction of methyl 2-(3-nitrobenzylidene)-acetoacetate with 2-(N-methyl-N-perfluorooctylsulphonylamino)-ethyl 3-aminocrotonate in methanol.

Yield: 33% of theory.

Example 40

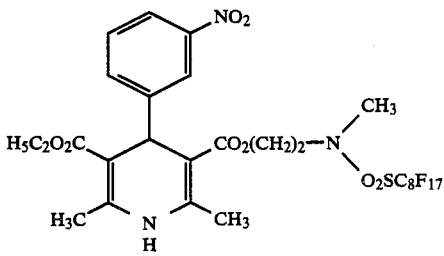

Ethyl 2-(N-methyl-N-perfluorooctylsulphonylamino)ethyl 1,4-dihydro-2,6-dimethyl-4-(3-nitrophenyl)-pyridine-3,5-dicarboxylate of melting point: 124° C. (isopropanol) was obtained analogously to Example 1 by reaction of ethyl 2-(3-nitrobenzylidene)-acetoacetate with 2-(N-methyl-N-perfluorooctylsulphonylamino)-ethyl 3-aminocrotonate in ethanol.

Yield: 35%.

Example 41

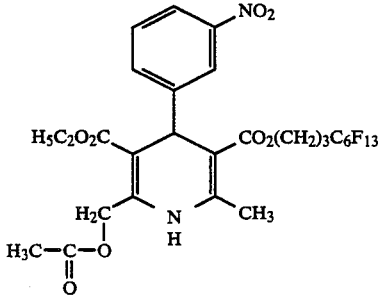

3-Ethyl 5-(3-perfluorohexyl-propyl) 1,4-dihydro-2-acetoxymethyl-6-methyl-4-(3-nitrophenyl)-pyridine-3,5-dicarboxylate of melting point: 78° C. (ether/petroleum ether) was obtained analogously to Example 1 by reaction of ethyl 4-acetoxy-2-(3-nitrobenzylidene)-acetoacetate with 3-perfluorohexyl-propyl 3-aminocrotonate in isopropanol.

Yield: 59% of theory.

Example 42

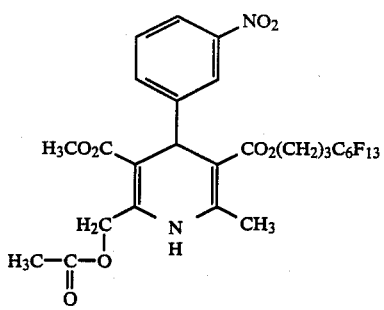

3-Methyl 5-(3-perfluorohexyl-propyl) 1,4-dihydro-2-acetoxymethyl-6-methyl-4-(3-nitrophenyl)-pyridine-3,5-dicarboxylate of melting point: 72° C. (ether/petroleum ether) was obtained analogously to Example 1 by reaction of methyl 4-acetoxy-2-(3-nitrobenzylidene)-acetoacetate with 3-perfluorohexyl-propyl 3-aminocrotonate in isopropanol.
Yield: 63% of theory.

Example 43

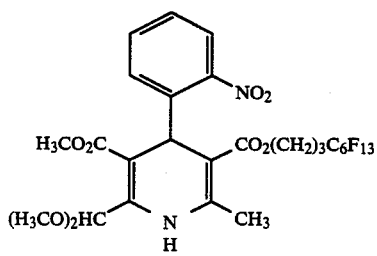

3-Methyl 5-(3-perfluorohexyl-propyl) 1,4-dihydro-2-dimethoxymethyl-6-methyl-4-(2-nitrophenyl)-pyridine-3,5-dicarboxylate was obtained as highly viscous oil (M+=752) analogously to Example 1 by reaction of methyl 4,4-dimethoxy-2-(2-nitrobenzylidene)-acetoacetate with 3-perfluorohexyl-propyl 3-aminocrotonate in methanol. Yield: 53% of theory.

Example 44

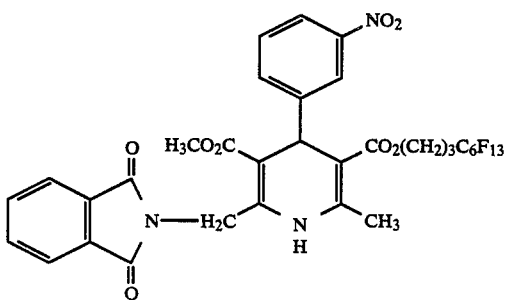

Methyl 4-phthalimido-2-(3-nitrobenzylidene)-acetoacetate was reacted with 3-perfluorohexyl-propyl 3-aminocrotonate in methanol analogously to Example 1. The solvent was then distilled off in vacuo and the residue was heated in toluene in the presence of catalytic amounts of p-toluenesulphonic acid using a water separator. Working up gave 3-methyl 5-(3-perfluorohexyl-propyl) 1,4-dihydro-2-phthalimidomethyl-6-methyl-4-(3-nitrophenyl)-pyridine-3,5-dicarboxylate of melting point: 132° C. (ether).
Yield: 48% of theory.

Example 45

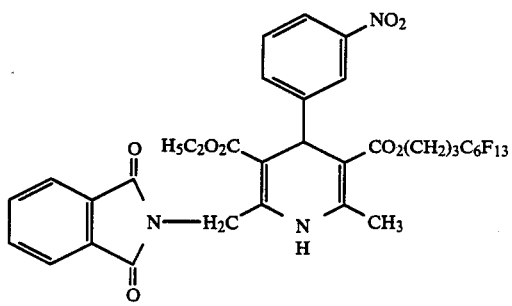

3-Ethyl 5-(3-perfluorohexyl-propyl) 1,4-dihydro-2-phthalimidomethyl-6-methyl-4-(3-nitrophenyl)-pyridine-3,5-dicarboxylate of melting point: 98° C. (ether) was prepared analogously to Example 44 from ethyl 4-phthalimido-2-(3-nitrobenzylidene)-acetoacetate and 3-perfluorohexylpropyl 3-aminocrotonate.
Yield: 52% of theory.

Example 46

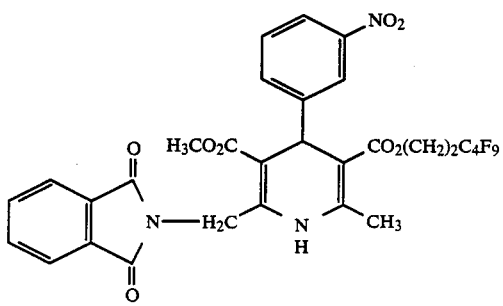

Methyl 2-perfluorobutyl-ethyl 1,4-dihydro-2-phthalimidomethyl-6-methyl-4-(3-nitrophenyl)-pyridine-3,5-dicarboxylate of melting point: 111° C. (ether) was prepared analogously to Example 44 from methyl 4-phthalimido-2-(3-nitrobenzylidene)-acetoacetate and 2-perfluorobutylethyl 3-aminocrotonate.
Yield: 45% of theory.

Example 47

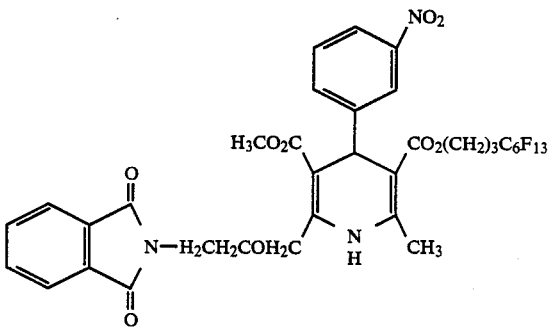

3-Methyl 5-(3-perfluorohexyl-propyl 1,4-dihydro-2-(2-phthalimidoethoxymethyl)-6-methyl-4-(3-nitrophenyl)pyridine-3,5-dicarboxylate of melting point: 99° C. (ether/petroleum ether) was obtained analogously to Example 1 by reaction of methyl 4-(2-phthalimidoethoxy)-2-(3-nitrobenzyilidene)-acetoacetate with 3-perfluorohexyl-propyl 3-aminocrotonate in isopropanol.

Yield: 42% of theory.

Example 48 (Process variant H)

3-Methyl 5-(3-perfluorohexyl-propyl 1,4-dihydro-2-(2-aminoethoxymethyl)-6-methyl-4-(3-nitrophenyl)-pyridine-3,5-dicarboxylate

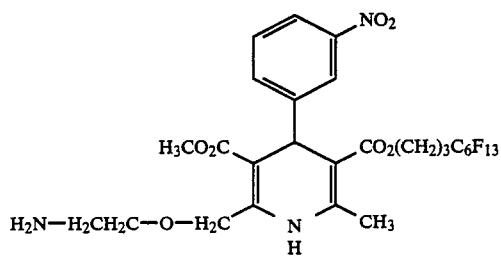

4.9 g (5.6 mmol) of 3-methyl 5-(3-perfluorohexylpropyl) 1,4-dihydro-2-(2-phthalimidoethoxy-methyl)-6-methyl-4-(3-nitrophenyl)-pyridine-3,5-dicarboxylate (Example 47) were heated under reflux together with 1.4 g (27 mmol) of hydrazine hydrate in 75 ml of ethanol for 30 minutes. The undissolved material was then filtered off, 300 ml of water were added to the filtrate and the mixture was extracted twice with 100 ml of methylene chloride each time. The organic phases were concentrated in vacuo, after drying over sodium sulphate, and the solid residue was purified by column chromatography over silica gel with methanol as the eluting agent and dried over diphosphorus pentoxide.

Melting point: 77°-78° C.

Yield: 1.8 g (44% of theory).

Example 49

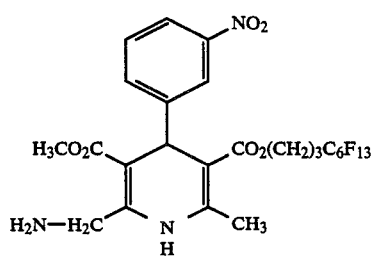

3-Methyl 5-(3-perfluorohexyl-propyl) 1,4-dihydro-2-aminomethyl-6-methyl-4-(3-nitrophenyl)-pyridine-3,5-dicarboxylate was obtained as a yellow oil analogously to Example 48 by reaction of 3-methyl 5-(3-perfluorohexylpropyl) 1,4-dihyro-2-phthalimidomethyl-6-methyl-4-(3-nitrophenyl)-pyridine-3,5-dicarboxylate (Example 44) with hydrazine in ethanol.

Yield: 39% of theory.

N (calculated) 5.9% N (found) 5.8%.

Example 50 (Process variant H)

3-Methyl 5-(3-perfluorohexyl-propyl) 1,4-dihydro-2-cyano-6-methyl-4-(2-nitrophenyl)-pyridine-3,5-dicarboxylate

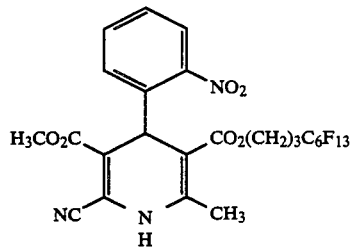

4 g (5.3 mmol) of 3-methyl 5-(3-perfluorohexylpropyl) 1,4-dihydro-2-dimethoxymethyl-6-methyl-4-(2-nitrophenyl)-pyridine-3,5-dicarboxylate (Example 43) were taken up in 100 ml of acetone and, after addition of 10 ml of 20% strength hydrochloric acid, the mixture was stirred at room temperature for 2 hours. The reaction mixture was then concentrated in vacuo, the residue was taken up in water and the aqueous phase was neutralized with sodium bicarbonate solution and extracted with methylene chloride. The organic extracts were concentrated under reduced pressure, after drying over anhydrous sodium sulphate, and 2 g (54%) of 3-methyl 5-(3-perfluorohexyl-propyl) 1,4-dihydro-2-formyl-6-methyl-4-(2-nitrophenyl)-pyridine-3,5-dicarboxylate resulted as a yellow oil, and the oil was taken up in 100 ml of glacial acetic acid and, after addition of 0.22 g of hydroxylamine hydrochloride and 0.42 g of sodium acetate, the mixture was stirred at room temperature for 3 hours. 24 ml of acetic anhydride and 5.5 g of sodium acetate were then added and the reaction mixture was heated under reflux for 24 hours. After cooling, the solvent was distilled off in vacuo, the residue was neutralized with sodium bicarbonate and the aqueous phase was extracted with ethyl acetate. The organic extracts were dried over anhydrous sodium sulphate and concentrated under reduced pressure and the residue was purified by column chromatography over silica gel with methylene chloride/ethyl acetate=4/1, to give 0.9 g (44%) of a yellow oil ($M^+=703$).

Example 51 (Process variant H)

3-Ethyl 5-(3-perfluorohexyl-propyl 1,4-dihydro-2-hydroxymethyl-6-methyl-4-(3-nitrophenyl)-pyridine-3,5-dicarboxylate

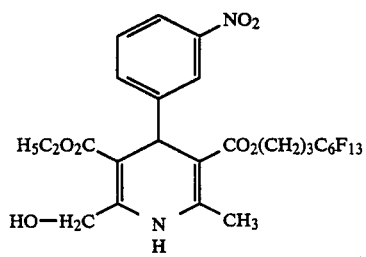

2 g (2.6 mmol) of 3-ethyl 5-(3-perfluorohexylpropyl), 1,4-dihydro-2-acetoxymethyl-6-methyl-4-(3-nitrophenyl)-pyridine-3,5-dicarboxylate (Example 41) were dissolved in 30 ml of methanol and, after addition of catalytic amounts of sodium methylate, the mixture was stirred at room temperature for 15 minutes. It was then neutralized with glacial acetic acid and the reaction mixture was concentrated in vacuo. The residue was taken up in methylene chloride and the organic phase was washed with water and dried over sodium sulphate. After evaporating off the solvent, the oily crude product was purified by column chromatography over silica gel with methylene chloride/ethanol=20/1, melting point: 124°–125° C.

Yield: 1 g (53% of theory).

Example 52

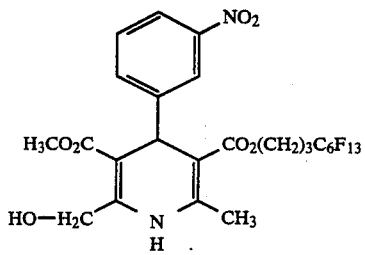

3-Methyl 5-(3-perfluorohexyl-propyl) 1,4-dihydro-2-hydroxymethyl-6-methyl-4-(3-nitrophenyl)-pyridine-3,5-dicarboxylate of melting point: 106° C. was obtained analogously to Example 51 by solvolysis of 3-methyl 5-(3-perfluorohexyl-propyl) 1,4-dihydro-2-acetoxymethyl-6-methyl-4-(3-nitrophenyl)-pyridine-3,5-dicarboxylate (Example 42).

Yield: 56% of theory.

It will be understood that the specification and examples are illustrative but not limitative of the present invention and that other embodiments within the spirit and scope of the invention will suggest themselves to those skilled in the art.

We claim:

1. A compound of the following formula

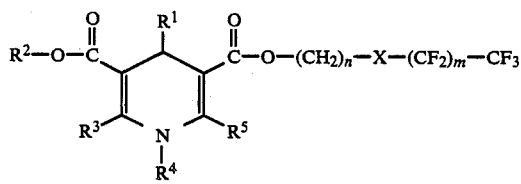

in which $R^1$ represents phenyl, pyridyl or benzoxadiazolyl, these ring systems being substituted by 1 or 2 identical or different substituents from the group consisting of chlorine, trifluoromethyl, nitro and cyano, $R^2$ represents a straight-chain, branched or cyclic hydrocarbon radical which has up to 8 carbon atoms and which is optionally interrupted by an oxygen atom in the chain and or which is optionally substituted by fluorine, cyano, acetoxy, phenyl, phenoxy or α-, β- or γ-pyridyl, or by an amino group, this amino group carrying two identical or different substituents from the group comprising alkyl with up to 4 carbon atoms and benzyl, $R^3$ and $R^5$ are identical or different and each represent a straight-chain or cyclic alkyl radical with up to 6 carbon atoms, or one of the substituents $R^3$ or $R^5$ represents alkyl radical which has up to 4 carbon atoms and is substituted by acetoxy, hydroxyl, phthalimido, amino, phthalimidoethoxy or aminoethoxy, or one of the substituents $R^3$ or $R^5$ represents the formyl or nitrile group, $R^4$ represents hydrogen or the morpholinoethyl radical, n is greater than/equal to 1 and m is greater than/equal to 1, and the sum of n and m representing an integer from 5 to 15, and x represents a single bond or the group —N(CH$_3$)O$_2$S—, or a pharmaceutically acceptable acid addition salt thereof.

2. A compound according to claim 1, wherein such compound is methyl 2-perfluorobutyl-ethyl 1,4-dihydro-2,6-dimethyl-4-(3-nitrophenyl)-pyridine-3,5-dicarboxylate of the formula

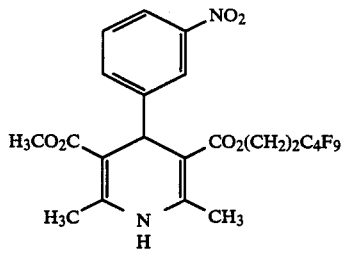

or a pharmaceutically acceptable acid addition salt thereof.

3. A compound according to claim 1, wherein such compound is methyl perfluorohexylmethyl 1,4-dihydro-2,6-dimethyl-4-(3-nitrophenyl)-pyridine-3,5-dicarboxylate of the formula

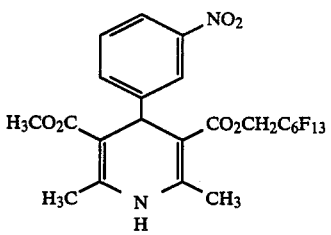

or a pharmaceutically acceptable acid addition salt thereof.

4. A compound according to claim 1, wherein such compound is methyl 2-perfluorohexyl-ethyl 1,4-dihydro-2,6-dimethyl-4-(3-nitrophenyl)-pyridine-3,5-dicarboxylate of the formula

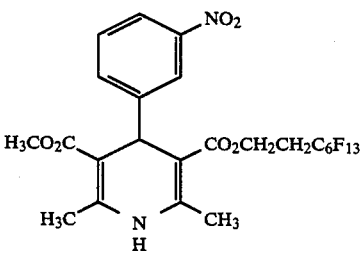

or a pharmaceutically acceptable acid addition salt thereof.

5. A compound according to claim 1, wherein such compound is methyl 3-perfluorohexyl-propyl 1,4-dihydro-2,6-dimethyl-4-(3-nitrophenyl)-pyridine-3,5-dicarboxylate of the formula

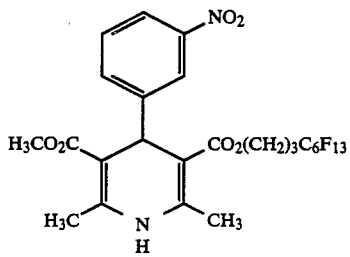

or a pharmaceutically acceptable acid addition salt thereof.

6. A compound according to claim 1, wherein such compound is methyl 3-perfluorohexyl-propyl (+)-1,4-dihydro-2,6-dimethyl-4-(3-nitrophenyl)-pyridine-3,5-dicarboxylate of the formula

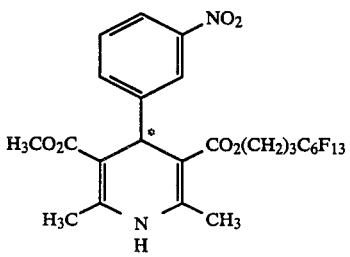

or a pharmaceutically acceptable acid addition salt thereof.

7. A compound according to claim 1, wherein such compound is methyl 3-perfluorohexyl-propyl 1,4-dihydro-2,6-dimethyl-4-(2-nitrophenyl)-pyridine-3,5-dicarboxylate of the formula

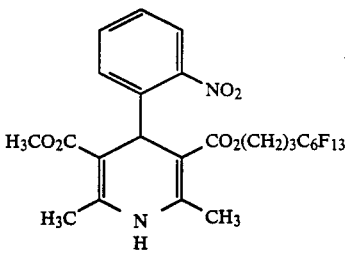

or a pharmaceutically acceptable acid addition salt thereof.

8. A hypotensive composition comprising a hypotensive amount of a compound or salt according to claim 1 and a diluent.

9. A unit dose of a composition according to claim 8 in the form of a tablet, capsule or ampule.

10. A method of combating hypertension in a patient which comprises administering to such patient a hypotensive amount of a compound or salt according to claim 1.

11. The method according to claim 10, wherein such compound is
    methyl 2-perfluorobutyl-ethyl 1,4-dihydro-2,6-dimethyl-4-(3-nitrophenyl)-pyridine-3,5-dicarboxylate,
    methyl perfluorohexylmethyl 1,4-dihydro-2,6-dimethyl-4-(3-nitrophenyl)-pyridine-3,5-dicarboxylate,
    methyl 2-perfluorohexyl-ethyl 1,4-dihydro-2,6-dimethyl-4-(3-nitrophenyl)-pyridine-3,5-dicarboxylate,
    methyl 3-perfluorohexyl-propyl 1,4-dihydro-2,6-dimethyl-4-(3-nitrophenyl)-pyridine-3,5-dicarboxylate,
    methyl 3-perfluorohexyl-propyl (+)-1,4-dihydro-2,6-dimethyl-4-(3-nitrophenyl)-pyridine-3,5-dicarboxylate or
    methyl 3-perfluorohexyl-propyl 1,4-dihydro-2,6-dimethyl-4-(2-nitrophenyl)-pyridine-3,5-dicarboxylate,
or a pharmaceutically acceptable acid addition salt thereof.

* * * * *

UNITED STATES PATENT AND TRADEMARK OFFICE
CERTIFICATE OF CORRECTION

PATENT NO. : 4,798,840

DATED : January 17, 1989

INVENTOR(S) : Egbert Wehinger, et al

It is certified that error appears in the above-identified patent and that said Letters Patent is hereby corrected as shown below:

| | |
|---|---|
| Col. 5, line 28 | Insert --x,--before "n" |
| Col. 5, line 48 | Delete "dihydropyrodine" and insert --dihydropyridine-- |
| Col. 5, line 49 | Delete "archiral" and substitute --achiral-- |
| Col. 22, line 18 | Delete "79" and substitute --70-- |
| Col. 22, line 63 | Delete "imidazol" and substitute --imidazolide-- |
| Col. 33, line 58 | Delete "propuyl" and substitute --propyl-- |

Signed and Sealed this

Twenty-first Day of November, 1989

Attest:

JEFFREY M. SAMUELS

Attesting Officer     Acting Commissioner of Patents and Trademarks